United States Patent [19]

Asakura et al.

[11] Patent Number: 5,977,331
[45] Date of Patent: *Nov. 2, 1999

[54] α-KETOGLUTARATE DEHYDROGENASE GENE

[75] Inventors: Yoko Asakura; Yoshihiro Usuda; Nobuharu Tsujimoto; Eiichiro Kimura; Chizu Abe; Yoshio Kawahara; Tsuyoshi Nakamatsu; Osamu Kurahashi, all of Kawasaki, Japan

[73] Assignee: Ajinomoto Co., Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/750,152
[22] PCT Filed: Jun. 7, 1995
[86] PCT No.: PCT/JP95/01131
§ 371 Date: Dec. 12, 1996
§ 102(e) Date: Dec. 12, 1996
[87] PCT Pub. No.: WO95/34672
PCT Pub. Date: Dec. 21, 1995

[30] Foreign Application Priority Data

Jun. 14, 1994 [JP] Japan ..... 6-131744

[51] Int. Cl.[6] ..... C07H 21/02; C12P 13/04; C12P 13/14; C12N 1/20
[52] U.S. Cl. ..... 536/23.1; 435/106; 435/110; 435/252.53
[58] Field of Search ..... 435/106, 110, 435/115, 252.32; 536/23.1, 24.3; 935/60, 72

[56] References Cited

U.S. PATENT DOCUMENTS

| | | | |
|---|---|---|---|
| 4,757,009 | 7/1988 | Sano et al. | 435/106 |
| 4,968,609 | 11/1990 | Ito et al. | 435/108 |
| 4,970,157 | 11/1990 | Hibino et al. | 435/189 |
| 4,980,285 | 12/1990 | Sano et al. | 435/108 |
| 5,017,481 | 5/1991 | Matsui et al. | 435/108 |
| 5,426,050 | 6/1995 | Moringa et al. | 435/252.32 |
| 5,498,532 | 3/1996 | Katsumata et al. | 435/106 |
| 5,516,660 | 5/1996 | Wagner et al. | 435/106 |
| 5,597,727 | 1/1997 | Kohama et al. | 435/252.32 |

FOREIGN PATENT DOCUMENTS

| | | |
|---|---|---|
| 1 296994 | 11/1989 | Japan . |
| 1106554 | 3/1968 | United Kingdom . |

OTHER PUBLICATIONS

Repetto et al., Molecular and Cellular Biology 9(6) : 2695–2705 (1989).

Carlsson et al., Gene 61:217–224 (1987).

Isamu Shiio et al., "Presence and Regulation of alpha–Ketoglutarate Dehydrogenase Complex in a Glutamate–Producing Bacterium, *Brevibacterium flavum*", Agric. Biol. Chem., vol. 44, No. 8, pp. 1897–1904, 1980.

Isamu Shiio et al, "Glutamate Metabolism in a Glutamate–producing Bacterium, *Brevibacterium flavum*", Agrig. Biol. Chem., vol. 46, No. 2, pp. 493–500, 1982.

Patent Abstract of Japan, vol. 14, No. 80 (C–0689), Feb. 15, 1990.

*Primary Examiner*—W. Gary Jones
*Assistant Examiner*—Ethan Whisenant
*Attorney, Agent, or Firm*—Oblon, Spivak, McClelland, Maier & Neustadt, P.C.

[57] ABSTRACT

Disclosed are coryneform L-glutamic acid-producing bacteria deficient in α-ketoglutarate dehydrogenase, a method of producing L-glutamic acid by using the bacteria, a gene coding for an enzyme having α-KGDH activity originating from coryneform L-glutamic acid-producing bacteria, recombinant DNA containing the gene, coryneform bacteria harboring the recombinant DNA, and a method of producing L-lysine by using bacteria harboring the recombinant DNA and having L-lysine productivity.

13 Claims, 1 Drawing Sheet

F I G. 1
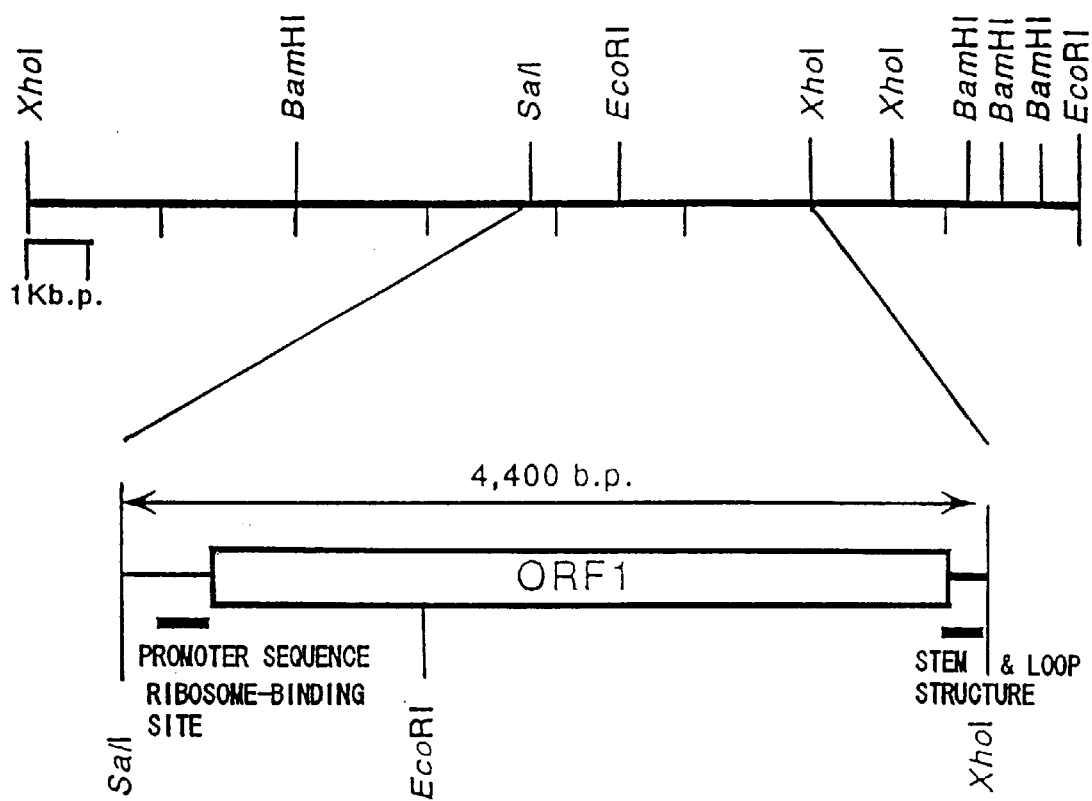

ନ# α-KETOGLUTARATE DEHYDROGENASE GENE

This application is a 371 of PCT/JP95/01131 filed Jun 7, 1995.

TECHNICAL FIELD

The present invention relates to breeding and utilization of coryneform bacteria used for fermentative production of L-glutamic acid and L-lysine. In particular, the present invention relates to coryneform L-glutamic acid-producing bacteria deficient in α-ketoglutarate dehydrogenase (α-KGDH), a method of producing L-glutamic acid by using the bacteria, a gene coding for an enzyme having α-KGDH activity (α-KGDH gene) originating from coryneform L-glutamic acid-producing bacteria, recombinant DNA containing the gene, coryneform bacteria harboring the recombinant DNA, and a method of producing L-lysine by using coryneform bacteria harboring the recombinant DNA and having L-lysine productivity.

BACKGROUND ART

L-Glutamic acid has been hitherto industrially produced by a fermentative method using coryneform bacteria belonging to the genus Brevibacterium or Corynebacterium.

Recently, it has been revealed that a mutant strain of *Escherichia coli*, in which the α-KGDH activity is deficient or lowered, and the glutamic acid-decomposing activity is lowered, has high L-glutamic acid productivity (Japanese Patent Laid-open No. 5-244970).

On the contrary, it was reported that a mutant strain having lowered α-KGDH activity had approximately the same L-glutamic acid productivity as that of its parent strain in the case of a bacterium belonging to the genus Brevibacterium (*Agric. Biol. Chem.*, 44, 1897 (1980), *Agric. Biol. Chem.*, 46, 493 (1982)). Therefore, it has been believed that the level of α-KGDH activity is not important for production of L-glutamic acid in coryneform bacteria.

On the other hand, it was found that a mutant strain of a L-glutamic acid-producing bacterium belonging to the genus Brevibacterium having lowered α-KGDH activity produces L-glutamic acid at high efficiency (maximum yield of 53%) when the bacterium is cultivated in a medium which contains a material containing an excessive amount of biotin as a carbon source without addition of materials which suppress an effect of biotin such as penicillins and surface active agents (Japanese Patent Laid-open No. 6-23779). However, since it has been believed that the level of α-KGDH activity is not important for production of L-gultamic acid in the coryneform bacteria as described above, there has been no example in which an α-KGDH gene of a coryneform L-glutamic acid-producing bacterium is cloned and analyzed. Further, mutant strains of coryneform bacteria being completely deficient in α-KGDH have been unknown.

DISCLOSURE OF THE INVENTION

An object of the present invention is to obtain an α-KGDH gene originating from coryneform L-glutamic acid-producing bacteria, prepare recombinant DNA containing the gene, clarify the influence of the level of α-KGDH activity on fermentative production of L-glutamic acid by using microorganisms transformed with the recombinant DNA, and thus provide a new methodology in breeding of coryneform L-glutamic acid-producing bacteria. More specifically, an object of the present invention is to obtain a coryneform L-glutamic acid-producing bacterium deficient in α-KGDH activity by destroying an α-KGDH gene existing on chromosomal DNA, and provide a method of producing L-glutamic acid by using the bacterium. Further, the present invention is contemplated to provide a coryneform bacterium harboring recombinant DNA containing an α-KGDH gene, and a method of producing L-lysine by using a coryneform bacterium harboring the recombinant DNA and having L-lysine productivity.

The present inventors have obtained an α-KGDH gene originating from a coryneform L-glutamic acid-producing bacterium, clarified its structure, transformed a coryneform L-glutamic acid-producing bacterium by using a plasmid into which the gene is incorporated, and investigated the level of α-KGDH activity and L-glutamic acid productivity of obtained transformants. As a result, it has been found that the α-KGDH activity remarkably affects production of L-glutamic acid. Further, the present inventors have found that a strain, in which the α-KGDH activity is deleted by destroying an α-KGDH gene existing on chromosome of a coryneform L-glutamic acid-producing bacterium, produces and accumulates a considerable amount of L-glutamic acid when it is cultivated in a medium containing an excessive amount of biotin without adding any substance for suppressing the action of biotin such as surfactant and penicillin. Furthermore, the present inventors have introduced recombinant DNA containing an α-KGDH gene into a coryneform bacterium having L-lysine productivity. As a result, it has been found that the L-lysine productivity of an obtained transformant is remarkably improved. Thus the present invention has been completed on the basis of these findings.

Namely, the present invention provides:

(1) a coryneform L-glutamic acid-producing bacterium deficient in α-KGDH activity due to occurrence of substitution, deletion, insertion, addition, or inversion of one or more nucleotides in a nucleotide sequence of a gene coding for an enzyme having α-KGDH activity or a promoter thereof existing on chromosome;

(2) a method of producing L-glutamic acid comprising the steps of cultivating the coryneform L-glutamic acid-producing bacterium described in the aforementioned item (1) in a liquid medium, to allow L-glutamic acid to be produced and accumulated in a culture liquid, and collecting it;

(3) an α-KGDH gene originating from a coryneform L-glutamic acid-producing bacterium;

(4) recombinant DNA obtained by ligating an α-KGDH gene originating from a coryneform L-glutamic acid-producing bacterium with a vector which functions in coryneform bacteria;

(5) a coryneform bacterium harboring the recombinant DNA described in the aforementioned item (4); and (6) a method of producing L-lysine comprising the steps of cultivating a coryneform bacterium harboring the recombinant DNA described in the aforementioned item (5) and having L-lysine productivity in a liquid medium, to allow L-lysine to be produced and accumulated in a culture liquid, and collecting it.

The present invention will be further explained in detail below.

The coryneform L-glutamic acid-producing bacteria referred to in the present invention include bacteria having been hitherto classified into the genus Brevibacterium but united into the genus Corynebacterium at present (*Int. J. Syst. Bacteriol.*, 41, 255 (1981)), and include bacteria belonging to the genus Brevibacterium closely relative to the genus Corynebacterium. Examples of such coryneform L-glutamic acid-producing bacteria include the followings.

Corynebacterium acetoacidophilum
Corynebacterium acetoglutamicum
Corynebacterium callunae
Corynebacterium glutamicum
Corynebacterium lilium (Corynebacterium glutamicum)
Corynebacterium melassecola
Brevibacterium divaricatum (Corynebacterium glutamicum)
Brevibacterium flavum (Corynebacterium glutamicum)
Brevibacterium immariophilum
Brevibacterium lactofermentum (Corynebacterium glutamicum)
Brevibacterium roseum
Brevibacterium saccharolyticum
Brevibacterium thiogenitalis
Corynebacterium thermoaminogenes Specifically, the following bacterial strains can be exemplified.

Corynebacterium acetoacidophilum ATCC 13870
Corynebacterium acetoglutamicum ATCC 15806
Corynebacterium callunae ATCC 15991
Corynebacterium glutamicum ATCC 13020
Corynebacterium lilium (Corynebacterium glutamicum) ATCC 15990
Corynebacterium melassecola ATCC 17965
Brevibacterium divaricatum (Corynebacterium glutamicum) ATCC 14020
Brevibacterium flavum (Corynebacterium glutamicum) ATCC 14067
Brevibacterium immariophilum ATCC 14068
Brevibacterium lactofermentum (Corynebacterium glutamicum) ATCC 13869
Brevibacterium roseum ATCC 13825
Brevibacterium saccharolyticum ATCC 14066
Brevibacterium thiogenitalis ATCC 19240
Corynebacterium thermoaminogenes AJ12340 (FERM BP-1539)

The α-KGDH gene of the present invention can be obtained as follows from chromosomal DNA of a wild strain of the coryneform L-glutamic acid-producing bacteria described above, or a mutant strain derived therefrom.

It is known that an α-KGDH complex of *Escherichia coli* is constituted by three subunits of E1 (α-ketoglutarate dehydrogenase: EC 1.2.4.2), E2 (dihydrolipoamide succinyltransferase: EC 2.3.1.61), and E3 (lipoamide dehydrogenase: 1.6.4.3), E1 and E2 genes form an operon structure, and E3 is shared with pyruvate dehydrogenase (EC 1.2.4.1). Nucleotide sequences of E1 and E2 genes of *Escherichia coli* have been clarified (*Eur. J. Biochem.*, 141, 351 (1984), *Eur. J. Biochem.*, 141, 361 (1984)).

Also for *Bacillus subtilis*, nucleotide sequences of E1 and E2 genes have been clarified (*J. Bacteriol.*, 171, 3667 (1989), *Gene*, 61, 217 (1987), etc.).

Thus by utilizing homology between the nucleotide sequences of the E1 genes of *Escherichia coli* and *Bacillus subtilis*, the present inventors have succeeded in isolation and cloning of an α-KGDH gene originating from a coryneform L-glutamic acid-producing bacterium. The following steps are provided therefor.

At first, a region having high homology between E1 subunit genes of α-KGDH of *Escherichia coli* and *Bacillus subtilis* is selected, and primers are synthesized according to sequences at both ends. Any of sequences is available as the primers provided that they satisfy conditions that they have random nucleotide compositions, have G+C contents of about 50%, form no special secondary structure, and are not complementary to one another. Those having a length of 20–30 nucleotides are usually used. Specifically, those shown in SEQ ID NOS:3 and 4 in Sequence Listing are exemplified.

Next, a probe comprising a part of an α-KGDH gene of *Bacillus subtilis* is prepared from the primers and *Bacillus subtilis* chromosomal DNA by using a polymerase chain reaction method (PCR method). Any probe having a length not less than about 20 nucleotides can be used, however, the probe desirably has a length not less than about 100 nucleotides. The probe desirably has a nucleotide sequence which is complementary to a sequence of an objective gene, however, those having high homology can be used.

On the other hand, chromosomal DNA of a coryneform L-glutamic acid-producing bacterium is extracted. DNA fragments obtained by digestion of the chromosomal DNA with a restriction enzyme are ligated with a vector to prepare recombinant DNA. The recombinant DNA is used to transform *Escherichia coli*. As the restriction enzyme, for example, BamHI, EcoRI, XhoI and so on are used. As the vector, those originating from *Escherichia coli*, for example, pUC19 and pBR322 are used. Any bacterial strain which is suitable for replication of vectors, is available as a recipient strain for the recombinant DNA. For example, bacterial strains of *Escherichia coli* such as HB101, JM109, and DH5 are used.

From transformants thus obtained, strains which hybridize with the probe DNA are selected by means of colony hybridization, and recombinant DNA is recovered from such transformants. Structures of restriction enzyme fragments of chromosomal DNA of the coryneform L-glutamic acid-producing bacterium ligated with the vector are analyzed.

An obtained DNA fragment does not necessarily contain an entire length of a gene coding for an objective enzyme. In such a case, the chromosomal DNA of the coryneform L-glutamic acid-producing bacterium is cut with another restriction enzyme, which is ligated with a vector to prepare recombinant DNA. The recombinant DNA is used to perform transformation. Selection by colony hybridization, and analysis of restriction enzyme fragments are performed in the same manner as described above. Thus a DNA fragment containing an entire length of the α-KGDH gene can be obtained. During this operation, the colony hybridization can be performed more easily by using the firstly obtained DNA fragment as a probe.

The DNA fragment containing the α-KGDH gene can be introduced into coryneform L-glutamic acid-producing bacteria after making recombination again with another appropriate vector. The vector to be used is, for example, a plasmid autonomously replicable in bacteria belonging to the genus Corynebacterium. Specifically, there are exemplified pAM330 (Japanese Patent Laid-open No. 58-67699), pHM1519 (Japanese Patent Laid-open No. 58-77895), pAJ655, pAJ611, pAJ1844 (Japanese Patent Laid-open No. 58-192900 for the three), pCG1 (Japanese Patent Laid-open No. 57-134500), pCG2 (Japanese Patent Laid-open No. 58-35197), pCG4, pCG11 (Japanese Patent Laid-open No. 57-183799), pHK4 (Japanese Patent Laid-open No. 5-7491) and the like.

In order to prepare the recombinant DNA by ligating the vector described above with the α-KGDH gene of the coryneform L-glutamic acid-producing bacterium, the vector is previously cut with a restriction enzyme. The cutting is performed with the same restriction enzyme as that used for cutting the chromosomal DNA. Alternatively, the cutting is performed with a restriction enzyme which produces cut faces complementary to cut faces of the chromosomal DNA fragment. Ligation is commonly performed by using a ligase such as T4 DNA ligase.

Introduction of various recombinant DNA into a recipient is conducted in accordance with a transformation method having been reported until now. For example, there is a method in which permeability of DNA is increased by treating recipient cells with calcium chloride (*J. Mol. Biol.*, 53, 159 (1970)) as reported for *Escherichia coli* K-12, and there is a method in which competent cells are prepared from cells in a propagating stage to introduce DNA as reported for *Bacillus subtilis* (*C. H. Gene*, 1, 153 (1977)). Alternatively, it is also possible to apply a method in which recombinant DNA is introduced into a DNA recipient after converting cells of the DNA recipient into a state of protoplasts or spheroplasts which easily incorporate recombinant DNA, as known for *Bacillus subtilis*, actinomycetes, and yeast (*Molec. Gen. Genet.*, 168, 111 (1979), *Nature*, 274, 398 (1978), *Proc. Natl. Acad. Sci. USA*, 75, 1929 (1978)).

In the protoplast method, a sufficiently high frequency can be obtained even in the case of the method used in *Bacillus subtilis* described above. However, as disclosed in Japanese Patent Laid-open No. 57-183799, it is also possible to utilize a method wherein DNA is incorporated in a state in which protoplasts of bacterial cells belonging to the genus Corynebacterium are brought into contact with divalent metal ion and one of polyethylene glycol and polyvinyl alcohol. Incorporation of DNA can be also facilitated by adding carboxymethyl cellulose, dextran, Ficoll, Bruronic F68 (produced by Selva Co.) and the like, instead of polyethylene glycol and polyvinyl alcohol. The method for transformation used in Examples of the present invention is an electric pulse method (see Japanese Patent Laid-open No. 2-207791).

A bacterial strain thus obtained, into which the recombinant DNA containing the α-KGDH gene originating from the coryneform L-glutamic acid-producing bacterium has been introduced, is cultivated in an ordinary medium containing a carbon source, a nitrogen source, inorganic salts, and optionally organic trace nutrients. Thus an enzyme having α-KGDH activity can be produced in cells at a high level.

Saccharide such as glucose, sucrose, waste molasses, and starch hydrolysate, as well as organic acids such as acetic acid and citric acid, and alcohols such as ethanol are used as the carbon source. Urea, ammonium salts, aqueous ammonia, ammonia gas and so on are used as the nitrogen source. Phosphates, potassium salts, magnesium salts, iron salts, manganese salts and so on are used as the inorganic salt. Amino acids, vitamins, fatty acids, nucleic acids, as well as peptone, yeast extract, soybean protein hydrolysate and so on containing them are used as the organic trace nutrient.

Cultivation is performed under an aerobic condition for 10–40 hours at a temperature of 25–37° C. while controlling pH at 5–9.

After completion of the cultivation, L-glutamic acid produced and accumulated in a culture liquid is quantitatively determined, and the level of α-KGDH activity of bacterial cells is measured. The activity can be measured in accordance with a method described in *Agric. Biol. Chem.*, 44, 1897 (1980) or the like using a sample obtained such that bacterial cells recovered from a culture through an operation of centrifugation or the like are ground by a sonication treatment, a French Press treatment or the like, subsequently cell debris is removed by centrifugation, and low molecular weight substances are removed by gel filtration.

Thus the relationship between the level of α-KGDH activity and the L-glutamic acid productivity has been investigated for the coryneform L-glutamic acid-producing bacterium with the amplified gene and a bacterium without the amplified gene. As a result, it has been revealed that the L-glutamic acid productivity decreases in the bacterium in which the level of α-KGDH activity is increased by amplification of the gene, as shown in Reference Example 1 described below.

Utilization of the gene of the present invention includes preparation of α-KGDH activity-deficient strains by insertion of a drug-relevant gene or the like, preparation of strains with weak activity by in vitro mutation, preparation of expression-lowered strains by modification of a promoter and so on, which makes it possible to efficiently breed a bacterial strain in which the L-glutamic acid productivity is further improved as compared with conventional coryneform L-glutamic acid-producing bacteria.

A strain deficient in α-KGDH activity can be obtained either by a method which uses a chemical reagent to induce mutation, or by a method which resides in genetic recombination. However, in the case of the method for introducing mutation by using a chemical reagent, it is relatively easy to obtain a strain in which the α-KGDH activity is lowered, but it is difficult to obtain a strain in which the activity is completely deficient. In order to obtain the latter strain, it is advantageous to use a method in which an α-KGDH gene existing on chromosome is modified or destroyed by means of a genetic homologous recombination method on the basis of the structure of the α-KGDH gene having been clarified as described above. Destruction of a gene by homologous recombination has been already established, for which it is possible to utilize a method which uses linear DNA, a method which uses a temperature-sensitive plasmid and so on.

Specifically, substitution, deletion, insertion, addition or inversion of one or a plurality of nucleotides is caused in a nucleotide sequence in a coding region or a promoter region of the α-KGDH gene by means of a site-directed mutagenesis method (Kramer, W and Frits, H. J., *Methods in Enzymology*, 154, 350 (1987)) or a treatment with a chemical reagent such as sodium hyposulfite and hydroxylamine (Shortle, D. and Nathans, D., *Proc. Natl. Acad. Sci. U.S.A.*, 75, 270 (1978)). The gene thus modified or destroyed is used to substitute a normal gene on chromosome. It is thereby possible to delete the activity of α-KGDH as a gene product, or extinguish transcription of the α-KGDH gene.

The site-directed mutagenesis method is a method which uses a synthetic oligonucleotide, which is a technique to make it possible to introduce optional substitution, deletion, insertion, addition or inversion into only optional limited base pairs. Upon the use of this method, at first a plasmid cloned and having an objective gene with a determined nucleotide sequence of DNA is denatured to prepare single strands. Subsequently a synthetic oligonucleotide complementary to a portion contemplated to cause mutation is synthesized. However, the synthetic oligonucleotide is not allowed to have a completely complementary sequence, but it is allowed to have optional nucleotide substitution, deletion, insertion, addition or inversion. The single strand DNA is then annealed with the synthetic oligonucleotide having optional nucleotide substitution, deletion, insertion, addition or inversion. A complete double strand plasmid is synthesized by using a Klenow fragment of DNA polymerase I and T4 ligase, and it is introduced into competent cells of *Escherichia coli*. Some of transformants thus obtained have plasmids containing genes in which the optional nucleotide substitution, deletion, insertion, addition or inversion is fixed. A similar method which enables introduction of mutation of a gene to provide modification or destruction includes a recombinant PCR method (*PCR Technology*, Stockton press (1989)).

On the other hand, the method which uses the chemical reagent treatment is a method in which a DNA fragment containing an objective gene is directly treated with sodium hyposulfite, hydroxylamine or the like, whereby mutation having nucleotide substitution, deletion, insertion, addition or inversion is randomly introduced into the DNA fragment.

The method for substituting a normal gene on chromosome of a coryneform L-glutamic acid-producing bacterium with the gene thus obtained by introduction of mutation to give modification or destruction includes a method which utilizes homologous recombination (*Experiments in Molecular Genetics*, Cold Spring Harbor Laboratory press (1972); Matsuyama, S. and Mizushima, S., *J. Bacteriol.*, 162, 1196 (1985)). In the homologous recombination, when a plasmid or the like including a sequence having homology to a sequence on chromosome is introduced into a bacterial cell, recombination takes place at a certain frequency at a portion of the sequence having homology, and the entire introduced plasmid is incorporated into the chromosome. When further recombination takes place thereafter at a portion of the sequence having homology on the chromosome, the plasmid is again separated from the chromosome and falls off. At this time, depending on a position at which the recombination takes place, a gene with introduced mutation is occasionally fixed on the chromosome, and an original normal gene is eliminated and falls off from the chromosome together with the plasmid. Selection of such bacterial strains makes it possible to obtain a bacterial strain in which a normal gene on the chromosome is substituted with a gene into which nucleotide substitution, deletion, insertion, addition or inversion is introduced to provide modification or destruction.

A coryneform L-glutamic acid-producing bacterium deficient in α-KGDH activity thus obtained is remarkably more excellent in L-glutamic acid productivity especially in a medium containing an excessive amount of biotin than strains having partially lowered α-KGDH activity.

In order to produce and accumulate L-glutamic acid by using the coryneform L-glutamic acid-producing bacterium deficient in α-KGDH activity, the bacterium is cultivated in a liquid medium containing a carbon source, a nitrogen source, inorganic ions, and other nutrients. Conventionally, when the cultivation is performed in a liquid medium containing an excessive amount of biotin, it has been necessary to add a substance for suppressing biotin action, that is penicillin such as penicillin G, F, K, O, V or X, or a surfactant comprising higher fatty acid such as sucrose monopalmitate and polyoxyethylene sorbitan monopalmitate or a derivative thereof to the medium, in order to produce L-glutamic acid at a high yield. However, when the coryneform L-glutamic acid-producing bacterium of the present invention deficient in α-KGDH activity is used, L-glutamic acid can be produced and accumulated at a high yield with high accumulation without adding any substance for suppressing biotin action as described above even if the cultivation is performed in a liquid nutrient medium containing a high concentration of biotin of 10–1000 μg/l.

Namely, as the carbon source, it is also possible to use raw materials containing excessive biotin such as sugar liquid from sweet potato and beet or waste molasses, in addition to glucose, fructose, saccharified starch solution, acetic acid, etc. Ammonium salts, aqueous ammonia, ammonia gas, urea, etc. which are used for ordinary L-glutamic acid fermentation, are used as the nitrogen source. Additionally, inorganic ions such as phosphates and magnesium salts are appropriately used, if necessary. Trace nutrients such as thiamine are appropriately added to the medium, if necessary.

The cultivation is preferably performed under an aerobic condition. The cultivation temperature is preferably controlled to 24–42° C., and pH is preferably controlled to 5–9 during cultivation. Inorganic or organic, acidic or alkaline substances, as well as urea, calcium carbonate, ammonia gas, etc. can be used for adjustment of pH.

The method for collecting L-glutamic acid from a culture liquid is carried out by suitably combining known methods such as ion exchange resin treatments and crystallization.

In order to improve the L-glutamic acid productivity, it is advantageous to enhance glutamic acid biosynthetic genes. Examples of enhancement of the glutamic acid biosynthesis system genes include phosphofructokinase in the glycolytic pathway (PFK, Japanese Patent Laid-open No. 63-102692), phosphoenolpyruvate carboxylase in the anaplerotic pathway (PEPC, Japanese Patent Laid-open Nos. 60-87788 and 62-55089), citrate synthase in the TCA cycle (CS, Japanese Patent Laid-open Nos. 62-201585 and 63-119688), aconitate hydratase (ACO, Japanese Patent Laid-open No. 62-294086), isocitrate dehydrogenase (ICDH, Japanese Patent Laid-open Nos. 62-166890 and 63-214189), glutamate dehydrogenase for amination reaction (GDH, Japanese Patent Laid-open No. 61-268185), and so on.

In order to obtain the genes described above, the following methods may be available.

(1) As a mutant strain in which mutation arises in an objective gene and a characteristic character is presented, a mutant strain is obtained wherein the character disappears by introducing the objective gene. A gene which complements the character of the mutant strain is obtained from chromosome of a coryneform bacterium.

(2) When an objective gene has been already obtained from another organism, and its nucleotide sequence has been clarified, the objective gene is obtained by a technique of hybridization using DNA in a region having high homology as a probe.

(3) When a nucleotide sequence of an objective gene is fairly clarified in detail, a gene fragment containing the objective gene is obtained by means of a PCR method (polymerase chain reaction method) using chromosome of a coryneform bacterium as a template.

The methods described above may be used as a method for obtaining chromosome used herein. Any host-vector system may be used provided that it is available for coryneform bacteria, for which those described above are used. In Examples of the present invention, the method of (3) described above has been used, which is effective for a case in which the nucleotide sequence has been already clarified.

When the gene is obtained in accordance with the methods of (2) and (3) described above, if an objective gene has no original promoter, the objective gene can be expressed by inserting a DNA fragment having promoter activity in coryneform bacteria into a position upstream from the objective gene. In order to enhance expression of the objective gene, it may be available to ligate the objective gene at a position downstream from a strong promoter. Strong promoters, which function in cells of coryneform bacteria, include lac promoter, tac promoter, trp promoter, etc. from *Escherichia coli* (Y. Morinaga, M. Tsuchiya, K. Miwa and K. Sano, *J. Biotech.*, 5, 305–312 (1987)). In addition, trp promoter from a bacterium belonging to the genus Corynebacterium is also a preferable promoter (Japanese Patent Laid-open No. 62-195294). In Examples of the present invention, trp promoter from a coryneform bacterium has been used for expression of the PEPC gene.

Amplification of the α-KGDH gene of the present invention is useful in coryneform bacteria having L-lysine productivity for improving their productivity.

Various artificial mutant strains have been hitherto used as L-lysine-producing bacteria. Their L-lysine productivity can be improved by using them as a host and allowing them to harbor the recombinant DNA of the present invention. Such artificial mutant strains include the following: a mutant strain which is resistant to S-(2-aminoethyl)-cysteine (hereinafter abbreviated as "AEC"); a mutant strain which requires an amino acid such as L-homoserine for its growth (Japanese Patent Publication Nos. 48-28078 and 56-6499); a mutant strain which exhibits resistance to AEC and requires an amino acid such as L-leucine, L-homoserine, L-proline, L-serine, L-arginine, L-alanine, and L-valine, (U.S. Pat. Nos. 3,708,395 and 3,825,472); an L-lysine-producing mutant strain which exhibits resistance to DL-α-amino-ε-caprolactam, α-amino-lauryllactam, aspartate analog, sulfa drug, quinoid, and N-lauroylleucine; an L-lysine-producing mutant strain which exhibits resistance to inhibitors for oxaloacetate decarboxylase or respiratory system enzymes (Japanese Patent Laid-open Nos. 50-53588, 50-31093, 52-102498, 53-9394, 53-86089, 55-9783, 55-9759, 56-32995, 56-39778, and Japanese Patent Publication Nos. 53-43591, 53-1833); an L-lysine-producing mutant strain which requires inositol or acetic acid (Japanese Patent Laid-open Nos. 55-9784 and 56-8692); an L-lysine-producing mutant strain which exhibits sensitivity to fluoropyruvate or temperature not less than 34° C. (Japanese Patent Laid-open Nos. 55-9783 and 53-86090); a mutant strain of Brevibacterium or Corynebacterium which exhibits resistance to ethylene glycol and produces L-lysine (see U.S. Pat. No. 4,411,997) and so on.

Specifically, the following strains can be exemplified.

*Brevibacterium lactofermentum* AJ12031 (FERM-BP 277, see Japanese Patent Laid-open No. 60-62994)

*Brevibacterium lactofermentum* ATCC 39134 (Japanese Patent Laid-open No. 60-62994)

*Corynebacterium glutamicum* AJ3463 (FERM-P 1987, Japanese Patent Publication No. 51-34477)

*Brevibacterium lactofermentum* AJ12435 (FERM BP-2294, U.S. Pat. No. 5,304,476)

*Brevibacterium lactofermentum* AJ12592 (FERM BP-3239, U.S. Pat. No. 5,304,476)

*Corynebacterium glutamicum* AJ12596 (FERM BP-3242, U.S. Pat. No. 5,304,476)

Introduction of the α-KGDH gene into such an L-lysine-producing bacterium may be performed through ligation with an appropriate vector as described above.

The medium to be used for L-lysine production is an ordinary medium containing a carbon source, a nitrogen source, inorganic ions, and optionally other organic trace nutrients. Saccharide such as glucose, lactose, galactose, fructose, and starch hydrolysate, alcohols such as ethanol and inositol, and organic acids such as acetic acid, fumaric acid, citric acid, and succinic acid can be used as the carbon source. Inorganic ammonium salts such as ammonium sulfate, ammonium chloride, and ammonium phosphate, organic nitrogen such as soybean hydrolysate, ammonia gas, aqueous ammonia, etc. can be used as the nitrogen source. Small amounts of potassium phosphate, magnesium sulfate, iron ion, manganese ion, etc. are added as the inorganic ion. Appropriate amounts of required substance such as vitamin $B_1$, yeast extract, etc. are desirably contained as the organic trace nutrient, if necessary.

The cultivation is preferably carried out under an aerobic condition for 16–72 hours. The cultivation temperature is controlled to 30–45° C., and pH is controlled to 5–8.5 during cultivation. Inorganic or organic, acidic or alkaline substances, as well as ammonia gas can be used for pH adjustment.

Collection of L-lysine from a fermented liquid can be usually carried out by combining known methods such as an ion exchange resin method, a precipitation method and so on.

BRIEF DESCRIPTION OF THE DRAWINGS

FIG. 1 is a restriction enzyme map of a DNA fragment containing an α-KGDH gene.

DESCRIPTION OF PREFERRED EMBODIMENTS

The present invention will be more concretely explained below with reference to Examples. For restriction enzymes, commercially available products (produced by Takara Shuzo Co., Ltd.) were used.

EXAMPLE 1

Isolation and Structural Determination of α-KGDH Gene (1) Preparation of Probe

A region having high homology between E1 subunit genes of α-KGDH of *Escherichia coli* and *Bacillus subtilis* was selected, and oligonucleotides shown in SEQ ID NOS:3 and 4 in Sequence Listing were synthesized by using a DNA synthesizer (Model 394 produced by Applied Biosystems) in accordance with a phosphoamidite method.

The oligonucleotides (0.25 μmole) as primers, chromosomal DNA of *Bacillus subtilis* NA64 (0.1 μg) prepared in accordance with an ordinary method (this strain was obtained from Bacillus Genetic Stock Center (Ohio University, the United States)) as a template, and Taq DNA polymerase (2.5 units) (produced by Takara Shuzo Co., Ltd.) were added to 0.1 ml of 10 mM Tris-HCl buffer (pH 8.3) containing each 200 μM of DATP, dCTP, dGTP, dTTP, 50 mM of potassium chloride, 1.5 mM of magnesium chloride, and 0.0001% of gelatin. A PCR method was performed in which a cycle comprising 1 minute at 94° C., 2 minutes at 55° C., and 3 minutes at 72° C. was repeated 30 times. A reaction solution was subjected to agarose gel electrophoresis, and an objective DNA fragment was recovered by using glass powder (produced by Takara Shuzo Co., Ltd.). The DNA fragment was labeled in accordance with an ordinary method of labeling by using a Klenow fragment (produced by Amersham) and [β-$^{32}$dCTP] (produced by Amersham), and used as a probe.

(2) Preparation of Chromosomal DNA Fragments of *Brevibacterium lactofermentum* ATCC13869

*Brevibacterium lactofermentum* ATCC13869 was inoculated to 500 ml of a T-Y medium (pH 7.2) comprising 1% Bacto Tryptone (made by Difco), 0.5% Bacto yeast extract (made by Difco), and 0.5% sodium chloride, and cultivated at 31.5° C. for 6 hours to obtain a culture. The culture was centrifuged at 5,000 rpm for 10 minutes, and 2 g of wet cell pellet was obtained as a precipitate.

Chromosomal DNA was extracted from the cell pellet in accordance with a method of Saito and Miura (*Biochem. Biophys. Acta.*, 72, 619 (1963)). The chromosomal DNA (2 μl) and a restriction enzyme EcoRI (200 units) were respectively mixed with 50 mM Tris-HCl buffer (pH 7.5) containing 10 mM magnesium chloride, 100 mM sodium chloride, and 1 mM dithiothreitol, and reacted at a temperature of 37° C. for 15 hours. After completion of the reaction, the solution was subjected to a phenol extraction treatment in accordance with an ordinary method, and subjected to an ethanol precipitation treatment to obtain chromosomal DNA fragments of *Brevibacterium lactofermentum* ATCC13869 digested with EcoRI.

(3) Isolation of α-KGDH Gene of *Brevibacterium lactofermentum* ATCC13869

A plasmid vector pUC18 (produced by Takara Shuzo Co., Ltd.) (1 μg) and a restriction enzyme EcoRI (20 units) were mixed with 50 mM Tris-HCl buffer (pH 7.5) containing 10 mM magnesium chloride, 100 mM sodium chloride, and 1 mM dithiothreitol, and reacted at a temperature of 37° C. for 2 hours to obtain a digested solution. The solution was subjected to phenol extraction and ethanol precipitation in accordance with an ordinary method. Subsequently, in order to prevent DNA fragments originating from the plasmid vector from religation, the DNA fragments were dephosphatized by means of a bacterial alkaline phosphatase treatment in accordance with a method of *Molecular Cloning*, 2nd edition (J. Sambrook, E. F. Fritsch and T. Maniatis, Cold Spring Harbor Laboratory Press, pl. 60 (1989)), followed by a phenol extraction treatment and ethanol precipitation in accordance with an ordinary method.

pUC18 thus digested with EcoRI (0.1 μg), the chromosomal DNA fragments of *Brevibacterium lactofermentum* ATCC13869 digested with EcoRI obtained in (2) (1 μg), and T4 DNA ligase (1 unit) (produced by Takara Shuzo Co., Ltd.) were added to 66 mM Tris-HCl buffer (pH 7.5) containing 6.6 mM magnesium chloride, 10 mM dithiothreitol, and 10 mM adenosine triphosphate, and reacted at a temperature of 16° C. for 8 hours to ligate DNA. Subsequently the DNA mixture was used to transform *Escherichia coli* JM109 (produced by Takara Shuzo Co., Ltd.) in accordance with an ordinary method, which was spread on an L agar medium containing 100 μg/ml of ampicillin to obtain about 10,000 transformants.

A transformant, which hybridized with the probe DNA obtained in (1), was selected from the obtained transformants in accordance with a method of *Molecular Cloning*, 2nd edition (J. Sambrook, E. F. Fritsch and T. Maniatis, Cold Spring Harbor Laboratory Press, pl. 90 (1989)).

(4) Determination of Nucleotide Sequence of α-KGDH Gene of *Brevibacterium lactofermentum* ATCC13869

Plasmid DNA was prepared from the transformant obtained in (3) in accordance with an alkaline bacteriolysis method described in *Molecular Cloning*, 2nd edition (J. Sambrook, E. F. Fritsch and T. Maniatis, Cold Spring Harbor Laboratory Press, pl. 25 (1989)). The plasmid DNA contained a DNA fragment of about 6 kilobases originating from chromosomal DNA of *Brevibacterium lactofermentum* ATCC13869. The plasmid was digested with restriction enzymes EcoRI and XhoI by using the reaction composition in (3), followed by agarose gel electrophoresis in accordance with an ordinary method. Southern hybridization was performed in the same manner as (3) to identify a fragment which hybridized with the probe DNA. As a result, it was revealed that a cut fragment of about 3 kilobases digested with EcoRI and XhoI hybridized. The DNA fragment was ligated with a plasmid vector pHS397 (produced by Takara Shuzo Co., Ltd.) digested with EcoRI and XhoI as done in (3), and cloned. Obtained plasmid DNA was used to determine the nucleotide sequence of the DNA fragment. Nucleotide sequence determination was performed in accordance with a method of Sanger (*J. Mol. Biol.*, 143, 161 (1980)) by using Taq DyeDeoxy Terminator Cycle Sequencing Kit (produced by Applied Biochemical).

Since the obtained DNA fragment did not contain a complete open reading frame, transformation was performed with a recombinant plasmid obtained by cutting chromosomal DNA of *Brevibacterium lactofermentum* ATCC13869 with XhoI, and ligating it with pHSG397 as done in (3). A hybridizing transformant was selected by using a probe obtained by labeling the EcoRI-XhoI cut fragment of about 3 kilobases originating from chromosomal DNA of *Brevibacterium lactofermentum* ATCC13869 obtained in (2) in accordance with the method in (1). A plasmid harbored by the obtained transformant contained a DNA fragment of about 9 kilobases. A restriction map of a gene containing the DNA fragment is shown in FIG. 1. The plasmid was digested with restriction enzyme SalI and XhoI by using the reaction composition in (3), followed by agarose gel electrophoresis in accordance with an ordinary method to identify the hybridizing fragment in accordance with the method in (3). As a result, a fragment of about 4.4 kilobases was revealed. The DNA fragment was ligated with a plasmid vector pHSG397 digested with SalI and XhoI as done in (3), and cloned. This plasmid was designated as pHSGS-X. A nucleotide sequence of a DNA fragment of about 1.4 kilobase from a SalI cut site to an EcoRI cut site in the SalI-XhoI cut fragment contained in the plasmid was determined in the same manner as described above.

The nucleotide sequence of the SalI-XhoI cut gene fragment thus obtained is as shown in SEQ ID NO:1 in Sequence Listing. An open reading frame has been estimated, and an amino acid sequence of a product deduced from its nucleotide sequence is shown in SEQ ID NOS:1 and 2 in Sequence Listing. Namely, the gene coding for a protein comprising the amino acid sequence shown in SEQ ID NO:1 in Sequence Listing is the α-KGDH gene of *Brevibacterium lactofermentum* ATCC13869. The methionine residue located at the N-terminal of a protein originates from ATG as a start codon, and thus it is often irrelevant to an original function of the protein. It is well-known that such a methionine residue is eliminated by the action of peptidase after translation. Accordingly, the protein mentioned above also has a possibility of occurrence of elimination of methionine residue.

The nucleotide sequence and the amino acid sequence were respectively compared with known sequences with respect to homology. Used data bases were EMBL and SWISS-PROT. As a result, it has been revealed that the DNA and the protein encoded by it shown in SEQ ID NO:1 in Sequence Listing are a novel gene and a novel protein in coryneform bacteria having homology to E1 subunit gene of α-KGDH and so on of *Escherichia coli* and *Bacillus subtilis* having been already reported.

The protein encoded by the gene of the invention comprises 1,257 amino acids including a methionine residue at the N-terminal, and has characteristics greatly different from those of α-KGDH already reported. Namely, about 900 amino acids on the C-terminal side exhibit high homology to various E1 subunits, however, 300 amino acids on the N-terminal side cannot be found in α-KGDH of other species, suggesting that the protein of the invention has a special function. By comparing the portion of 300 amino acid on the N-terminal side with known sequences for homology, the portion has been found to have homology to E2 subunit of *Escherichia coli* and bacteria belonging to the genus Azotobacter. This suggests a possibility that the protein of the invention is different from α-KGDH of other species, and has both activities of E1 and E2.

In addition, sequences (281–286 and 307–312) similar to common promoter sequences found in *Escherichia coli*, and a sequence (422–428) similar to a ribosome-binding sequence of coryneform bacteria have been found at positions upstream from the open reading frame of the gene of the invention. A stem & loop structure (4243–4281) similar to a transcription termination signal has been found at a position downstream from the open reading frame of the gene of the invention. These sequences suggest that the gene of the invention independently undergoes transcription and translation, and has a genetic structure different from those of α-KGDH of other species.

EXAMPLE 2

Amplification of α-KGDH Activity by Expression of α-KGDH Gene Originating from *Brevibacterium lactofermentum* ATCC13869

(1) Introduction of α-KGDH Gene Into *Brevibacterium lactofermentum* ATCC 13869 and AJ11060

The pHSGS-X plasmid DNA (1 μg) obtained in Example 1, and restriction enzymes SalI and XhoI (each 20 units) were mixed in the buffer described in (3) in Example 1, and reacted at a temperature of 37° C. for 3 hours. On the other hand, plasmid pPK4 (refer to Japanese Patent Laid-open No. 5-7491) DNA (1 μg) autonomously replicable in bacteria belonging to the genus Brevibacterium and SalI (20 units) were mixed in the buffer described in (3) in Example 1, and reacted at a temperature of 37° C. for 3 hours. The both reaction solutions were subjected to phenol extraction and ethanol precipitation in accordance with an ordinary method. Subsequently, in order to prevent DNA fragments originating from the plasmid vector from religation, the DNA fragments were dephosphatized by means of a bacterial alkaline phosphatase treatment by using the method of Example 1 (3), followed by a phenol extraction treatment and ethanol precipitation in accordance with an ordinary method. pPK4 (0.1 μg) digested with SalI, pHSGS-X plasmid DNA (0.5 μg) digested with SalI and XhoI obtained as described above, and T4 DNA ligase (produced by Takara Shuzo Co., Ltd.) (1 unit) were mixed in the buffer described in Example 1 (3), and reacted at a temperature of 16° C. for 8 hours to ligate DNA. Next, the DNA mixture was introduced into *Brevibacterium lactofermentum* AJ11060 (Japanese Patent Publication No. 59-10797) in accordance with an ordinary method of transformation using an electric pulse method (Japanese Patent Laid-open No. 2-207791). An obtained solution was spread on an agar medium comprising 1% polypeptone, 1% yeast extract, 0.5% sodium chloride, 0.5% glucose, and 25 μg/ml kanamycin to obtain a transformant AJ11060/pPKS-X. This transformant was designated as *Brevibacterium lactofermentum* AJ12999, and deposited in National Institute of Bioscience and Human Technology of Agency of Industrial Science and Technology (1–3, Higashi 1-chome, Tsukuba-shi, Ibaraki-ken 305, Japan) on Jun. 3, 1994, as deposition number of FERM P-14349, and transferred from the original deposition to international deposition based on Budapest Treaty on Jun. 2, 1995, and has been deposited as deposition number of FERM BP-5123.

Plasmid DNA was extracted from the obtained transformant in accordance with Example 1 (4), and agarose gel electrophoresis was performed in accordance with an ordinary method. Thus recombinant DNA was selected in which the SalI-XhoI fragment originating from *Brevibacterium lactofermentum* ATCC13869 was ligated with the plasmid pPK4. The obtained plasmid was designated as pPKS-X.

A transformant ATCC 13869/pPKS-X was obtained in the same manner using *Brevibacterium lactofermentum* ATCC 13869 as a host.

(2) Enzyme Activity of Strain with Amplified α-KGDH Gene

*Brevibacterium lactofermentum* AJ11060/pPKS-X and ATCC 13869/pPKS-X obtained in (1) were inoculated to 50 ml of a medium (pH 8.0) comprising 8% glucose, 0.1% potassium dihydrogenphosphate, 0.004% magnesium sulfate, 3% ammonium sulfate, 0.001% ferrous sulfate, 0.001% manganese sulfate, 0.05% soybean hydrolysate solution, 200 μg/l vitamin $B_1$, 300 μg/l biotin, 5% calcium carbonate, and 25 mg/l kanamycin, and cultivated at 31.5° C. for 18 hours. The culture liquid was centrifuged in accordance with an ordinary method, and cell pellet was collected.

The cell pellet was washed by repeating twice an operation comprising suspending the cell pellet in a 0.2% potassium chloride solution, and performing centrifugation. The cell pellet was suspended in a 0.1 M buffer (pH 7.7) of N-Tris(hydroxymethyl)methyl-2-amino ethanesulfonic acid (hereinafter referred to as TES) containing 30% glycerol, and treated with sonication, followed by centrifugation at 15,000 rpm for 30 minutes to obtain a supernatant. This cell lysate was subjected to Sephadex G-25 (produced by Pharmacia) column chromatography, and low molecular weight substances were eliminated to prepare a crude enzyme solution.

The α-KGDH activity of the obtained crude enzyme solution was measured as an increase in absorbance at 365 nm of 3-acetylpyridine adenine dinucleotide by using a reaction solution of a composition described in *Agric. Biol. Chem.*, 44, 1987 (1980). The protein concentration of the crude enzyme solution was measured by using a kit produced by Bio-Rad using bovine serum albumin as a standard, and the specific activity of the enzyme was calculated. As controls, specific activities were determined for AJ11060/pPK4 and ATCC 13869/pPK4 obtained by transformation with the plasmid pPK4 in the same manner. Results are shown in Table 1. AJ11060/pPKS-X and ATCC 13869/pPKS-X respectively had specific activities which were twice or more specific activities of AJ11060/pPK4 and ATCC 13869/pPK4. According to the results, it has been proved that the obtained gene fragment codes for an enzyme having the α-KGDH activity.

TABLE 1

| Bacterial strain | α-KGDH specific activity (ΔAbs/min/mg protein) |
|---|---|
| AJ11060/pPK4 | 0.029 |
| AJ11060/pPKS-X | 0.055 |
| ATCC 13869/pPK4 | 0.019 |
| ATCC 13869/pPKS-X | 0.060 |

As a result of SDS polyacrylamide gel electrophoresis of the crude enzyme solution, amplification of a band of about 135 kilodalton was observed corresponding to a molecular weight of 139 kilodalton of the enzyme expected for the obtained gene. This indicates that the obtained gene is actually expressed in the transformed strain.

Reference Example 1

Relationship Between α-KGDH Activity and L-glutamic Acid Productivity

*Brevibacterium lactofermentum* AJ11060/pPK4 and AJ11060/pPKS-X were cultivated in an L-glutamic acid-producing medium, and L-glutamic acid produced and accumulated in a culture liquid was measured. The cultivation was performed as follows by using a method in which a surfactant was added.

A production medium (pH 8.0, 20 ml) comprising 8% glucose, 0.1% potassium dihydrogenphosphate, 0.04% magnesium sulfate, 3% ammonium sulfate, 0.001% ferrous sulfate, 0.001% manganese sulfate, 1.5% soybean hydrolysate solution, 200 μg/l thiamine hydrochloride, 300 μg/l biotin, 25 mg/l kanamycin, and 5% $CaCO_3$ (separately sterilized) was dispensed and poured into a Sakaguchi flask having a volume of 500 ml, and sterilized by heating. Bacterial cells previously obtained by cultivating AJ11060/pPK4 and AJ11060/pPKS-X respectively on a plate medium (pH 7.2) comprising 1% polypeptone (produced by Nippon Seiyaku), 1% Bacto yeast extract (produced by Difco), 0.5% sodium chloride, 0.5% glucose, and 25 mg/l kanamycin were inoculated to the medium, and cultivated at 31.5° C. for 18 hours with shaking to obtain a seed culture.

The obtained seed culture was inoculated in an amount of 5% to a production medium added with 3 g/l of a surfactant (Tween 40: produced by Sigma) and a production medium without the surfactant, and cultivated at 31.5° C. for 20 hours in the same manner.

After completion of the cultivation, the amount of accumulated L-glutamic acid and the remaining glucose concentration in a culture liquid were measured by using a Biotech Analyzer AS-210 produced by Asahi Chemical Industry Co., Ltd. The growth amount of bacterial cells was determined by measuring absorbance at 620 nm of a solution obtained by diluting a culture 51-fold with 0.02 N hydrochloric acid. Results are shown in Table 2.

TABLE 2

| Strain | Surfactant | Growth (OD) | Remaining sugar (g/dl) | Accumulation amount (g/dl) | Yield (%) |
|---|---|---|---|---|---|
| AJ11060/pPK4 | − | 1.72 | 0.45 | 0 | 0 |
|  | + | 0.78 | 1.80 | 2.46 | 42.4 |
| AJ11060/pPKS-X | − | 1.31 | 1.89 | 0 | 0 |
|  | + | 0.78 | 3.69 | 0.37 | 9.4 |

Production of L-glutamic acid was not found at all in any of the bacterial strains in the medium in which no surfactant was added. L-glutamic acid was produced and accumulated in the culture liquid only when the surfactant was added. In this experiment, the yield of L-glutamic acid was remarkably decreased in the strain into which the plasmid pPKS-X containing the α-KGDH gene was introduced, as compared with the pPK4-introduced strain as a control. This fact demonstrates that the level of α-KGDH activity greatly affects the production of L-glutamic acid based on the addition of the surfactant.

Reference Example 2

Comparison of L-glutamic Acid Productivity by Penicillin Addition Method

The effect of α-KGDH gene amplification on L-glutamic acid production was investigated by means of a penicillin addition method.

A seed culture was prepared in the same manner as Reference Example 1. The seed culture was inoculated respectively to a production medium added with 0.4 unit/ml of penicillin and a production medium added with no penicillin so that the dry weight of cell pellet was about 2%, and cultivated at 31.5° C. for about 25 hours with shaking.

After completion of the cultivation, the amount of accumulated L-glutamic acid and the remaining glucose concentration in a culture liquid were measured in the same manner as Reference Example 1. Results are shown in Table 3. The results demonstrate that the level of α-KGDH activity also greatly affects L-glutamic acid production by the addition of penicillin.

TABLE 3

| Strain | Penicillin | Growth amount (OD) | Remaining sugar (g/dl) | Accumulation amount (g/dl) | Yield (%) |
|---|---|---|---|---|---|
| AJ11060/pPK4 | − | 1.84 | 0.0 | 0 | 0 |
|  | + | 0.72 | 0.0 | 3.90 | 49.1 |
| AJ11060/pPKS-X | − | 1.87 | 0.0 | 0 | 0 |
|  | + | 1.07 | 0.0 | 2.39 | 30.1 |

EXAMPLE 3

Preparation of α-KGDH Gene-Deficient Strain

According to the fact that the production of L-glutamic acid was suppressed by amplification of the α-KGDH gene, it was expected, on the contrary, that the yield of glutamic acid could be improved by destroying the α-KGDH gene. A gene-destroyed strain was obtained by a homologous recombination method using a temperature-sensitive plasmid described in Japanese Patent Laid-open No. 5-7491. Specifically, the α-KGDH gene has two sites digested by KpnI therein at 1340th and 3266th positions in SEQ ID NO:1 in Sequence Listing. Thus pHSGS-X obtained in Example 1 was partially digested with KpnI, and then self-ligated to prepare a plasmid pHSGS-XΔK which was deficient in 1926 base pairs of a KpnI fragment. The α-KGDH gene on pHSGS-XΔK has a structure lacking a central portion. Next, a mutant type replication origin, which was obtained from a plasmid autonomously replicable in coryneform bacteria and had temperature-sensitive autonomous replicability, was introduced into a BamHI recognition site of pHSGS-XΔK to prepare a plasmid pBTS-XΔK. Specifically, a plasmid pHSC4 (Japanese Patent Laid-open No. 5-7491), which was obtained from a plasmid autonomously replicable in coryneform bacteria and had temperature-sensitive autonomous replicability, was digested with a restriction enzyme KpnI, blunt-ended by using a DNA blunt end formation kit (produced by Takara Shuzo Co., Ltd., Blunting kit), and then ligated with a BamHI linker (produced by Takara Shuzo Co., Ltd.), followed by self-ligation to obtain a plasmid which was digested with a restriction enzyme BamHI to prepare a gene fragment containing a mutant type replication origin in which the autonomous replicability was temperature-sensitive. The gene fragment was introduced into a BamHI site of PHSGS-XΔK to prepare a plasmid pBTS-XΔK.

This plasmid was introduced into Brevibacterium lactofermentum ATCC 13869 as a wild strain of a coryneform L-glutamic acid-producing bacterium by using an electric pulse method (Japanese Patent Laid-open No. 2-207791), and an α-KGDH gene on chromosome was substituted with the deficient type by using a method described in Japanese Patent Laid-open No. 5-7491. Specifically, ATCC 13869/pBTS-XΔK, in which the plasmid was introduced, was cultivated in an CM2G liquid medium (1% polypeptone, 1% yeast extract, 0.5% NaCl, 0.5% glucose, pH 7.2) at 25° C.

for 6 hours with shaking, subsequently spread on an CM2G agar medium containing 5 μg/ml of chloramphenicol, and cultivated at 34° C. to form colonies which were obtained as plasmid-incorporated strains. A strain, which was sensitive to chloramphenicol at 34° C., was obtained from the strains by using a replica method. A nucleotide sequence of the α-KGDH gene on chromosome was investigated by using the sensitive strain, and it was confirmed that the α-KGDH gene was substituted into the deficient type. The strain was designated as AS strain. When the α-KGDH activity of the AS strain was measured in accordance with the method described in Example 2, no activity was detected at all.

EXAMPLE 4

Preparation of Plasmids for Amplifying gdh, gltA and icd Genes (1) Cloning of gdh, gltA and icd Genes Genes of gdh, gltA and icd of *Brevibacterium lactofermentum* were cloned by using a PCR method. Primers used for the PCR method were synthesized on the basis of sequences of gdh gene (*Molecular Microbiology*, 6(3), 317–326 (1992)), gltA gene (*Microbiology*, 140, 1817–1828 (1994)), and icd gene (*J. Bacteriol.*, 177, 774–782 (1995)) of *Corynebacterium glutamicum* already reported. Oligonucleotides shown in SEQ ID NOS:5 (5' side) and 6 (3' side) in Sequence Listing as primers for amplifying the gdh gene, oligonucleotides shown in SEQ ID NOS:7 (5' side) and 8 (3' side) as primers for amplifying the gltA gene, and oligonucleotides shown in SEQ ID NOS:9 (5' side) and 10 (3' side) as primers for amplifying the icd gene were respectively synthesized and used.

Chromosomal DNA was prepared from *Brevibacterium lactofermentum* ATCC13869 in accordance with the method in Example 1, which was used as a template to perform the PCR method using the aforementioned oligonucleotides as primers. Obtained amplified products were blunt-ended at their both ends by using a commercially available DNA blunt end formation kit (produced by Takara Shuzo Co., Ltd., Blunting kit), and then cloned into a SmaI site of a vector plasmid pHSG399 (produced by Takara Shuzo Co., Ltd.) respectively to obtain plasmids pHSG-gdh, pHSG-gltA, and pHSG-icd.

(2) Cloning and Expression of ppc Gene

Chromosomal DNA of *Brevibacterium lactofermentum* ATCC 13869 was prepared in accordance with the method in Example 1, and it was used as a template to obtain a DNA fragment of about 3.4 Kbp containing ppc gene coding for PEPC by using the PCR method. Primers used for the PCR method were synthesized on the basis of a sequence of ppc gene of *Corynebacterium glutamicum* already reported (*Gene*, 77, 237–251 (1989)), and the PCR reaction was performed in the same manner as described above. Sequences of the primers are shown in SEQ ID NOS:11 (5' side) and 12 (3' side).

An amplified product of the PCR reaction was digested with a restriction enzyme SalI (produced by Takara Shuzo Co., Ltd.), and inserted into a SalI site of a plasmid pHSG399 to obtain a plasmid pHSG-ppc'. PEPC gene of pHSG-ppc' is inserted in a direction opposite to that of lac promoter of pHSG399.

Next, a promoter of tryptophan operon known as a promoter to function in *Brevibacterium lactofermentum* (*Gene*, 53, 191–200 (1987)) was inserted at a position upstream from the ppc gene on pHSG-ppc'. It is known that this promoter has a sequence comprising 51 nucleotides shown in SEQ ID NO:13 in Sequence Listing, and it exhibits the activity. A nucleotide strand having the sequence shown in SEQ ID NO:13 and a nucleotide strand having a sequence of SEQ ID NO:14 as its complementary strand were synthesized so that double strand DNA containing the 51 base pairs having the promoter activity with both ends corresponding to cut fragments by restriction enzymes KpnI and XbaI are obtained.

The both synthesized DNA were mixed to give a concentration of 10 pmol/μg for each, heated at 100° C. for 10 minutes, and then left and cooled at room temperature to cause annealing. pHSG-ppc' was digested with restriction enzymes KpnI and XbaI (produced by Takara Shuzo Co., Ltd.), and ligated with the promoter described above. The ligation reaction was performed by using a ligation kit produced by Takara Shuzo Co., Ltd. Thus a plasmid pHSG-ppc, in which one copy of the promoter of the tryptophan operon was inserted at a position upstream from the ppc gene, was obtained.

(3) Preparation of Plasmid Constructed by Ligating Three Species of Genes of gdh, gltA and icd A plasmid was prepared in which three species of the genes of gdh, gltA and icd were ligated. Specifically, the plasmid pHSG-gdh was digested with a restriction enzyme EcoRI, and blunt-ended by using a commercially available DNA blunt end formation kit (produced by Takara Shuzo Co., Ltd., Blunting kit), with which the PCR-amplified product of the gltA gene with both ends blunt-ended as described above was ligated to obtain a plasmid pHSG-gdh+gltA. Further, the plasmid pHSG-gdh+gltA was digested with a restriction enzyme KpnI, and blunt-ended in the same manner, with which the PCR-amplified product of the icd gene with both ends blunt-ended as described above was ligated to obtain a plasmid pHSG-gdh+gltA+icd.

(4) Preparation of Plasmid Constructed by Ligating Three Species of Genes of gdh, gltA and ppc A plasmid was prepared in which three species of the genes of gdh, gltA and ppc were ligated. Specifically, the plasmid pHSG-gdh+gltA was digested with a restriction enzyme KpnI. The plasmid pHSG-ppc was digested with restriction enzymes KpnI and SalI to obtain a ppc gene fragment having the promoter of tryptophan operon at an upstream position. The obtained fragment was blunt-ended by using a DNA blunt end formation kit (produced by Takara Shuzo Co., Ltd., Blunting kit), and then inserted into a KpnI site of the plasmid pHSG-gdh+gltA by using a KpnI linker (produced by Takara Shuzo Co., Ltd.) to obtain a plasmid pHSG-gdh+gltA+ppc.

(5) Introduction of Replication Origin for Corynebacterium Into the Plasmids Described Above In order to allow pHSG-gdh, pHSG-gltA, pHSG-ppc, pHSG-icd, pHSG-gdh+gltA+icd, and pHSG-gdh+gltA+ppc to conduct autonomous replication in cells of coryneform bacteria, a replication origin (Japanese Patent Laid-open No. 5-7491) originating from a plasmid pHM1519 autonomously replicable in coryneform bacteria (*Agric. Biol. Chem.*, 48, 2901–2903 (1984)) already obtained was introduced into pHSG-gdh, pHSG-gltA, pHSG-ppc, pHSG-icd, pHSG-gdh+gltA+icd, and pHSG-gdh+gltA+ppc. Specifically, a plasmid pHK4 (Japanese Patent Laid-open No. 5-7491) having the replication origin originating from pHM1519 was digested with restriction enzymes BamHI and KpnI, and a gene fragment containing the replication origin was obtained. The obtained fragment was blunt-ended by using a DNA blunt end formation kit (produced by Takara Shuzo Co., Ltd., Blunting kit), and then inserted into KpnI sites of pHSC-gdh, pHSG-gltA, pHSG-ppc, and pHSG-icd respectively by using a KpnI linker (produced by Takara Shuzo Co., Ltd.) to obtain pGDH, pGLTA, pPPC, and pICD.

Further, the replication origin originating from pHM1519 was inserted into pHSG-gdh+gltA+icd and pHSG-gdh+gltA+ppc respectively at their SalI sites similarly using a SalI linker (produced by Takara Shuzo Co., Ltd.) to obtain pGDH+GLTA+ICD and pGDH+GLTA+PPC. In addition, pSAC4 was also prepared as a control, using a plasmid pHSG399 having none of these genes, in which the replication origin originating from pHM1519 was inserted into its SalI site similarly using a SalI linker (produced by Takara Shuzo Co., Ltd.).

EXAMPLE 7

Confirmation of Expression of Each Gene on pGDH, pGLTA pPPC, pICD, pGDH+GLTA+ICD, and pGDH+GLTA+PPC It was confirmed whether or not each of the genes on pGDH, pGLTA, pPPC, pICD, pGDH+GLTA+ICD, and pGDH+GLTA+PPC was expressed in cells of *Brevibacterium lactofermentum*, and these plasmids functioned for gene amplification. Specifically, each of the plasmids was introduced into *Brevibacterium lactofermentum* ATCC 13869 by means of an electric pulse method (Japanese Patent Laid-open No. 2-207791). Obtained transformants were selected by using a CM2G plate medium containing 10 g of polypeptone, 10 g of yeast extract, 5 g of glucose, 5 g of NaCl, and 15 g of agar in 1 l of pure water (pH 7.2) and containing 4 μg/ml of chloramphenicol. The obtained transformants were cultivated on a CM2G agar medium, inoculated to a medium containing 80 g of glucose, 1 g of $KH_2PO_4$, 0.4 g of $MgSO_4$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 μg of thiamine hydrochloride, 300 μg of biotin, and 50 g of $CaCO_3$ in 1 l of pure water (with pH adjusted to 8.0 with KOH), and cultivated at 31.5° C. for 16 hours. The culture liquid was centrifuged in accordance with an ordinary method, and bacterial cells were collected.

Crude extracts obtained by grinding the bacterial cells were used to measure GDH activities of ATCC 13869/pGDH, ATCC 13869/pGDH+GLTA+ICD, and ATCC 13869/pGDH+GLTA+PPC in accordance with a method described in *Molecular Microbiology*, 6(3), 317–326 (1992). As a result, it was found that each of these transformants had about 13-fold GDH activity as compared with ATCC 13869/pSAC4 as a control (Table 4). The CS activity of ATCC 13869/pGLTA, ATCC 13869/GDH+CLTA+ICD, and ATCC 13869/pGDH+GLTA+PPC was measured in accordance with a method described in *Microbiology*, 140, 1817–1828 (1994). The ICDH activity of ATCC 13869/pICD and ATCC 13869/GDH+GLTA+ICD was measured in accordance with a method described in *J. Bacteriol*, 177, 774–782 (1995). The PEPC activity of ATCC 13869/pPPC and ATCC 13869/pGDH+GLTA+PPC was measured in accordance with a method described in *Gene*, 77, 237–251 (1989). Results of measurement are shown in Tables 5–7. It was found that any transformant had about 2 to 20-fold activity of the objective enzyme as compared with ATCC 13869/pSAC4 as a control. According to this fact, it has been confirmed that each of the genes on pGDH, pGLTA, pPPC, pICD, pGDH+GLTA+ICD, and pGDH+GLTA+PPC is expressed in cells of *Brevibacterium lactofermentum*, and executes its function.

TABLE 4

| Bacterial strain | GDH activity (ΔAbs/min/mg protein) |
| --- | --- |
| ATCC 13869/pGDH | 1.36 |
| ATCC 13869/pGDH+GLTA+ICD | 1.28 |
| ATCC 13869/pGDH+GLTA+PPC | 1.33 |
| ATCC 13869/pSAC4 | 0.11 |

TABLE 5

| Bacterial strain | CS activity (μmole/min/mg protein) |
| --- | --- |
| ATCC 13869/pGLTA | 5.5 |
| ATCC 13869/pGDH+GLTA+ICD | 4.8 |
| ATCC 13869/pGDH+GLTA+PPC | 4.8 |
| ATCC 13869/pSAC4 | 0.7 |

TABLE 6

| Bacterial strain | PEPC activity (units/min/mg protein) |
| --- | --- |
| ATCC 13869/pPPC | 1.12 |
| ATCC 13869/pGDH+GLTA+PPC | 1.04 |
| ATCC 13869/pSAC4 | 0.11 |

TABLE 7

| Bacterial strain | ICDH activity (units/min/mg protein) |
| --- | --- |
| ATCC 13869/pICD | 3.5 |
| ATCC 13869/pGDH+GLTA+ICD | 2.8 |
| ATCC 13869/pSAC4 | 1.0 |

EXAMPLE 8

L-glutamic Acid Production by ΔS Strain, and ΔS Strains with Amplified gdh, gltA, ppc and icd Genes (1) Evaluation of L-glutamic Acid Production by ΔS Strain by Using Jar Fermenter A medium (300 ml) containing 60 g of glucose, 1 g of $KH_2PO_4$, 0.4 g of $MgSO_4$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 μg of thiamine hydrochloride, and 450 μg of biotin in 1 l of pure water was added to a jar fermenter having a volume of 1 l, and sterilized by heating. Bacterial cells of the ΔS strain obtained by cultivation on a CM2G agar medium were inoculated thereto, and cultivated at 31.5° C. for 30 hours while adjusting pH to 7.0, 7.2 or 7.5 with ammonia gas.

After completion of the cultivation, the bacterial cell concentration and the amount of L-glutamic acid accumulated in the medium were measured. Biotech Analyzer AS-210 produced by Asahi Chemical Industry Co., Ltd. was used for quantitative determination of L-glutamic acid. The bacterial cell concentration was measured in accordance with absorbance at 660 nm ($OD_{660}$) of a culture liquid diluted 51 times with pure water. Results are shown in Table 8.

TABLE 8

| pH | Bacterial cell concentration (OD) | L-glutamic acid (g/l) |
|---|---|---|
| 7.0 | 0.84 | 35 |
| 7.2 | 0.85 | 34 |
| 7.5 | 1.07 | 32 |

It was confirmed that the ΔS strain produced and accumulated L-glutamic acid at a high yield although it was cultivated in the medium containing an excessive amount of biotin.

(2) Evaluation of L-glutamic Acid Production by ΔS Strain, and ΔS Strains with Amplified gdh, gltA, ppc and icd Genes by Cultivation in Jar Farmentor pGDH, PGLTA, pPPC, pICD, pGDH+GLTA+ICD, or pGDH+GLTA+PPC prepared as described above was introduced into the ΔS strain to evaluate L-glutamic acid productivity of transformants in which each of the plasmids was introduced. Introduction of the plasmids into cells of *Brevibacterium lactofermentum* was performed in accordance with an electric pulse method (Japanese Patent Laid-open No. 2-207791). Obtained transformants were selected by using a CM2G plate medium containing 10 g of polypeptone, 10 g of yeast extract, 5 g of glucose, 5 g of NaCl, and 15 g of agar in 1 l of pure water (pH 7.2) and containing 4 μg/ml of chloramphenicol.

Evaluation of L-glutamic acid productivity of the ΔS strain and the obtained transformants was performed as described in the aforementioned item(1).

The bacterial cell concentration and the amount of L-glutamic acid accumulated in the medium after the cultivation were measured in the same manner as described above. Results are shown in Table 9.

TABLE 9

| Strain | Cell concentration (OD) | L-glutamic acid (g/l) |
|---|---|---|
| ΔS | 0.84 | 35 |
| ΔS/pGDH | 1.01 | 35 |
| ΔS/pGLTA | 0.83 | 37 |
| ΔS/pICD | 0.83 | 37 |
| ΔS/pPPC | 0.75 | 37 |
| ΔS/pGDH+GLTA+ICD | 0.95 | 38 |
| ΔS/pGDH+GLTA+PPC | 0.85 | 40 |
| ΔS/pSAC4 | 0.83 | 35 |

EXAMPLE 9

Production of L-lysine by L-lysine-Producing Bacterium with Amplified α-KGDH Gene pPKS-X and pPK4 prepared as described above were respectively introduced into *Brevibacterium lactofermentum* AJ12435 (FERM BP-2294) exhibiting resistance to S-(2-aminoethyl)-L-cysteine and having L-lysine productivity derived by mutation from *Brevibacterium lactofermentum* ATCC 13869, and their L-lysine productivity was evaluated. Introduction of the plasmids was performed by using an electric pulse method (Japanese Patent Laid-open No. 2-207791). Transformants were selected by using a CM2G plate medium containing 10 g of polypeptone, 10 g of yeast extract, 5 g of glucose, 5 g of NaCl, and 15 g of agar in 1 l of pure water (pH 7.2) and containing 25 μg/ml of kanamycin.

Evaluation of L-lysine productivity was performed as follows. A medium (20 ml each) containing 100 g of glucose, 1 g of $KH_2PO_4$, 0.4 g of $MgSO_4$, 30 g of $(NH_4)_2SO_4$, 0.01 g of $FeSO_4 \cdot 7H_2O$, 0.01 g of $MnSO_4 \cdot 7H_2O$, 15 ml of soybean hydrolysate solution, 200 μg of thiamine hydrochloride, 300 μg of biotin, 25 mg of kanamycin, and 50 g of $CaCO_3$ in 1 l of pure water (with pH adjusted to 7.0 with KOH) was dispensed and poured into a flask having a volume of 500 ml, and sterilized by heating. Bacterial cells of AJ12435/pPK4 and AJ12435/pPKS-X obtained by cultivation on a CM2G plate medium containing 4 mg/l of kanamycin were inoculated thereto, and cultivated at 37° C. for 20 hours. After completion of the cultivation, the amount of L-lysine produced and accumulated in a culture liquid and the bacterial cell concentration were measured. Results are shown in Table 10.

TABLE 10

| Strain | L-lysine (g/l) | Cell concentration (OD) |
|---|---|---|
| AJ12435/pPK4 | 26 | 1.15 |
| AJ12435/pPKS-X | 31 | 0.92 |

Industrial Applicability

It has been revealed that the level of α-KGDH activity of coryneform L-glutamic acid-producing bacteria affects fermentative production of L-glutamic acid. Therefore, it becomes possible to efficiently breed bacterial strains having further improved L-glutamic acid productivity as compared with conventional coryneform L-glutamic acid-producing bacteria, by preparing α-KGDH gene activity-deficient strains by insertion of drug-relevant genes and so on, by preparing activity-leaky strains by in vitro mutation, and by preparing strains with lowered expression by modification of promoters and so on.

What is claimed is:

1. An isolated gene comprising 1) a nucleotide sequence which codes for an enzyme having the amino acid sequence shown in SEQ ID NO: 2 or 2) a nucleotide sequence which codes for an enzyme having substitution, deletion, or insertion of one or more amino acid residues in the amino acid sequence shown in SEQ ID NO: 2 and increases α-ketoglutarate dehydrogenase activity to produce succinyl-CoA from α-ketoglutarate in a coryneform L-glutamic acid-producing bacterium when alone introduced into the coryneform L-glutamic acid producing bacterium.

2. The gene according to claim 1, wherein the enzyme has the amino acid sequence shown in SEQ ID NO: 2.

3. A recombinant DNA obtained by ligating a gene comprising a nucleotide sequence which codes for an enzyme having the amino acid sequence shown in SEQ ID NO: 2 or an amino acid sequence having substitution, deletion, or insertion of one or more amino acid residues in the amino acid sequence shown in SEQ ID NO: 2 and increases α-ketoglutarate dehydrogenase activity to produce succinyl-CoA from α-ketoglutarate in a coryneform L-glutamic acid-producing bacterium when alone introduced into the coryneform L-glutamic acid-producing bacterium, with a vector which functions in coryneform bacteria.

4. A coryneform bacterium harboring the recombinant DNA according to claim 3.

5. A method of producing L-lysine comprising the steps of cultivating a coryneform bacterium harboring the recombinant DNA according to claim 3 and having L-lysine productivity in a liquid medium, to allow L-lysine to be produced and accumulated in a culture liquid, and collecting the L-lysine.

6. A recombinant DNA according to claim 3, wherein said enzyme has the amino acid sequence shown in SEQ ID NO: 2.

7. The coryneform bacterium according to claim 4, wherein said enzyme has the amino acid sequence shown in SEQ ID NO:2.

8. The method according to claim 5, wherein said enzyme has the amino acid sequence shown in SEQ ID NO: 2.

9. A mutant coryneform bacterium having higher L-glutamic acid productivity than the wild-type coryneform bacterium, wherein the mutant bacterium is deficient in α-ketoglutarate dehydrogenase activity, wherein the mutant bacterium has a mutation in the wild-type sequence of a gene encoding an enzyme having α-ketoglutarate dehydrogenase activity or in a promoter region thereof.

10. The mutant coryneform bacterium of claim 9, wherein the mutation is substitution, deletion, addition or inversion of one or more nucleotides in the wild-type sequence of the gene encoding an enzyme having α-ketoglutarate dehydrogenase activity or in a promoter region thereof.

11. The mutant coryneform bacterium of claim 9, wherein wild-type enzyme having α-ketoglutarate dehydrogenase activity has the amino acid sequence of SEQ ID NO: 2.

12. The mutant coryneform bacterium of claim 9, wherein the wild-type sequence of the gene encoding an enzyme having α-ketoglutarate dehydrogenase has the nucleotide sequence of SEQ ID NO: 1.

13. A method of producing L-glutamic acid, comprising culturing the mutant coryneform bacterium of the claim 9 in a liquid culture medium to produce L-glutamic acid and isolating the L-glutamic acid.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 4394 base pairs
      (B) TYPE: nucleic acid
      (C) STRANDEDNESS: double
      (D) TOPOLOGY: linear (ii) MOLECULE TYPE: genomic DNA (iii) HYPOTHETICAL: NO (iv) ANTI-SENSE: NO (vi) ORIGINAL SOURCE:
    (A) ORGANISM: Brevibacterium lactofermetum
    (B) STRAIN: ATCC13869

(ix) FEATURE:
    (A) NAME/KEY: CDS
    (B) LOCATION: 443..4213

(ix) FEATURE:
    (A) NAME/KEY: -35 signal
    (B) LOCATION: 281..287

(ix) FEATURE:
    (A) NAME/KEY: -10 signal
    (B) LOCATION: 307..312

(ix) FEATURE:
    (A) NAME/KEY: RBS
    (B) LOCATION: 421..428

(ix) FEATURE:
    (A) NAME/KEY: terminator
    (B) LOCATION: 4243..4281

(xi) SEQUENCE DESCRIPTION: SEQ ID NO:1:

```
GTCGACAAGC AAAATCGAAG CGGCAGCACG CCGCGTCGGA GCCTTAAACG CCATCGCCGC      60

CATCCCTGAT GGTTTCAATC ATCAAGTCGG TGAACGCGGG CGCAACCTGT CATCCGGACA     120

GCGCCAACTG ATCGCGCTGG CGCGCGCCGA ACTCATCGAG CCTTCCATCA TGCTTCTCGA     180

CGAAGCCACC TCCACCCTCG ACCCCGCCAC CGAAGCCGTT ATCCTCAACG CCTCCGATCG     240

AGTCACTAAG GGACGCACCA GCATCATCGT CGCGCACCGC TTGGCAACCG CTAAAAGGGC     300

CGACCGTATT CTTGTTGTTG AACAAGGACG TATCATTGAG GACGGATCTC ACGACGCGTT     360

GTTGTCTGCT AACGGCACCT ACGCCCGCAT GTGGCATTTA ATGGCCTGAC ACGTTATTTT     420

TAGGAGAACT GTCAACAAAT TA ATG CTA CAA CTG GGG CTT AGG CAT AAT CAG      472
                         Met Leu Gln Leu Gly Leu Arg His Asn Gln
                          1               5                  10

CCA ACG ACC AAC GTT ACA GTG GAT AAA ATA AAG CTC AAT AAA CCC TCA       520
Pro Thr Thr Asn Val Thr Val Asp Lys Ile Lys Leu Asn Lys Pro Ser
            15                  20                  25

AGA AGC AAG GAA AAG AGG CGA GTA CCT GCC GTG AGC AGC GCT AGT ACT       568
Arg Ser Lys Glu Lys Arg Arg Val Pro Ala Val Ser Ser Ala Ser Thr
        30                  35                  40

TTC GGC CAG AAT GCG TGG CTG GTA GAC GAG ATG TTC CAG CAG TTC CAG       616
Phe Gly Gln Asn Ala Trp Leu Val Asp Glu Met Phe Gln Gln Phe Gln
    45                  50                  55

AAG GAC CCC AAG TCC GTG GAC AAG GAA TGG AGA GAA CTC TTT GAG GCG       664
Lys Asp Pro Lys Ser Val Asp Lys Glu Trp Arg Glu Leu Phe Glu Ala
60                  65                  70

CAG GGG GGA CCA AAT GCT ACC CCC GCT ACA ACA GAA GCA CAG CCT TCA       712
Gln Gly Gly Pro Asn Ala Thr Pro Ala Thr Thr Glu Ala Gln Pro Ser
75                  80                  85                  90

GCG CCC AAG GAG TCT GCG AAA CCA GCA CCA AAG GCT GCC CCT GCA GCC       760
Ala Pro Lys Glu Ser Ala Lys Pro Ala Pro Lys Ala Ala Pro Ala Ala
                95                  100                 105

AAG GCA GCA CCG CGC GTA GAA ACC AAG CCG GCC GCC AAG ACC GCC CCT       808
Lys Ala Ala Pro Arg Val Glu Thr Lys Pro Ala Ala Lys Thr Ala Pro
            110                 115                 120

AAG GCC AAG GAG TCC TCA GTG CCA CAG CAA CCT AAG CTT CCG GAG CCA       856
Lys Ala Lys Glu Ser Ser Val Pro Gln Gln Pro Lys Leu Pro Glu Pro
        125                 130                 135
```

-continued

| | |
|---|---|
| GGA CAA ACC CCA ATC AGG GGT ATT TTC AAG TCC ATC GCG AAG AAC ATG<br>Gly Gln Thr Pro Ile Arg Gly Ile Phe Lys Ser Ile Ala Lys Asn Met<br>140                       145                     150 | 904 |
| GAT ATC TCC CTG GAA ATC CCA ACC GCA ACC TCG GTT CGC GAT ATG CCA<br>Asp Ile Ser Leu Glu Ile Pro Thr Ala Thr Ser Val Arg Asp Met Pro<br>155                     160                     165                  170 | 952 |
| GCT CGC CTC ATG TTC GAA AAC CGC GCG ATG GTC AAC GAT CAG CTC AAG<br>Ala Arg Leu Met Phe Glu Asn Arg Ala Met Val Asn Asp Gln Leu Lys<br>                   175                     180                     185 | 1000 |
| CGC ACC CGC GGT GGC AAG ATC TCC TTC ACC CAC ATC ATT GGC TAC GCC<br>Arg Thr Arg Gly Gly Lys Ile Ser Phe Thr His Ile Ile Gly Tyr Ala<br>         190                     195                     200 | 1048 |
| ATG GTG AAG GCA GTC ATG GCT CAC CCG GAC ATG AAC AAC TCC TAC GAC<br>Met Val Lys Ala Val Met Ala His Pro Asp Met Asn Asn Ser Tyr Asp<br>         205                     210                     215 | 1096 |
| GTC ATC GAC GGC AAG CCA ACC CTG ATC GTG CCT GAG CAC ATC AAC CTG<br>Val Ile Asp Gly Lys Pro Thr Leu Ile Val Pro Glu His Ile Asn Leu<br>220                     225                     230 | 1144 |
| GGC CTT GCC ATC GAC CTT CCT CAG AAG GAC GGC TCC CGC GCA CTT GTC<br>Gly Leu Ala Ile Asp Leu Pro Gln Lys Asp Gly Ser Arg Ala Leu Val<br>235                     240                     245                  250 | 1192 |
| GTA GCA GCC ATC AAG GAA ACC GAG AAG ATG AAC TTC TCC GAG TTC CTC<br>Val Ala Ala Ile Lys Glu Thr Glu Lys Met Asn Phe Ser Glu Phe Leu<br>                   255                     260                     265 | 1240 |
| GCA GCA TAC GAA GAC ATC GTG ACA CGC TCC CGC AAG GGC AAG CTC ACC<br>Ala Ala Tyr Glu Asp Ile Val Thr Arg Ser Arg Lys Gly Lys Leu Thr<br>         270                     275                     280 | 1288 |
| ATG GAT GAC TAC CAG GGC GTT ACC GTT TCC TTG ACC AAC CCA GGT GGC<br>Met Asp Asp Tyr Gln Gly Val Thr Val Ser Leu Thr Asn Pro Gly Gly<br>         285                     290                     295 | 1336 |
| ATC GGT ACC CGC CAC TCT GTC CCA CGT CTG ACC AAG GGC CAG GGC ACC<br>Ile Gly Thr Arg His Ser Val Pro Arg Leu Thr Lys Gly Gln Gly Thr<br>300                     305                     310 | 1384 |
| ATC ATC GGT GTC GGT TCC ATG GAT TAC CCA GCA GAG TTC CAG GGC GCT<br>Ile Ile Gly Val Gly Ser Met Asp Tyr Pro Ala Glu Phe Gln Gly Ala<br>315                     320                     325                  330 | 1432 |
| TCC GAA GAC CGC CTT GCA GAG CTC GGC GTT GGA AAG CTT GTC ACC ATC<br>Ser Glu Asp Arg Leu Ala Glu Leu Gly Val Gly Lys Leu Val Thr Ile<br>                   335                     340                     345 | 1480 |
| ACC TCC ACC TAC GAT CAC CGC GTG ATC CAG GGT GCT GTG TCC GGT GAA<br>Thr Ser Thr Tyr Asp His Arg Val Ile Gln Gly Ala Val Ser Gly Glu<br>         350                     355                     360 | 1528 |
| TTC CTG CGT ACC ATG TCT CGC CTG CTC ACC GAT GAT TCC TTC TGG GAT<br>Phe Leu Arg Thr Met Ser Arg Leu Leu Thr Asp Asp Ser Phe Trp Asp<br>         365                     370                     375 | 1576 |
| GAG ATC TTC GAC GCA ATG AAC GTT CCT TAC ACC CCA ATG CGT TGG GCA<br>Glu Ile Phe Asp Ala Met Asn Val Pro Tyr Thr Pro Met Arg Trp Ala<br>380                     385                     390 | 1624 |
| CAG GAC GTT CCA AAC ACC GGT GTT GAT AAG AAC ACC CGC GTC ATG CAG<br>Gln Asp Val Pro Asn Thr Gly Val Asp Lys Asn Thr Arg Val Met Gln<br>395                     400                     405                  410 | 1672 |
| CTC ATT GAG GCA TAC CGC TCC CGT GGA CAC CTC ATC GCT GAC ACC AAC<br>Leu Ile Glu Ala Tyr Arg Ser Arg Gly His Leu Ile Ala Asp Thr Asn<br>                   415                     420                     425 | 1720 |
| CCA CTT TCA TGG GTT CAG CCT GGC ATG CCA GTT CCA GAC CAC CGC GAC<br>Pro Leu Ser Trp Val Gln Pro Gly Met Pro Val Pro Asp His Arg Asp<br>         430                     435                     440 | 1768 |
| CTC GAC ATC GAG ACC CAC AGC CTG ACC ATC TGG GAT CTG GAC CGT ACC<br>Leu Asp Ile Glu Thr His Ser Leu Thr Ile Trp Asp Leu Asp Arg Thr<br>445                     450                     455 | 1816 |

```
TTC AGC GTC GGT GGC TTC GGC GGC AAG GAG ACC ATG ACC CTG CGC GAG        1864
Phe Ser Val Gly Gly Phe Gly Gly Lys Glu Thr Met Thr Leu Arg Glu
460                 465                 470

GTA CTG TCC CGC CTG CGC GCT GCC TAC ACC TTG AAG GTC GGC TCC GAA        1912
Val Leu Ser Arg Leu Arg Ala Ala Tyr Thr Leu Lys Val Gly Ser Glu
475                 480                 485                 490

TAC ACC CAC ATC CTG GAC CGC GAC GAG CGC ACC TGG CTG CAG GAC CGC        1960
Tyr Thr His Ile Leu Asp Arg Asp Glu Arg Thr Trp Leu Gln Asp Arg
            495                 500                 505

CTC GAA GCC GGA ATG CCA AAG CCA ACC CAG GCA GAG CAG AAG TAC ATC        2008
Leu Glu Ala Gly Met Pro Lys Pro Thr Gln Ala Glu Gln Lys Tyr Ile
                510                 515                 520

CTG CAG AAG CTG AAC GCC GCA GAG GCT TTC GAG AAC TTC CTG CAG ACC        2056
Leu Gln Lys Leu Asn Ala Ala Glu Ala Phe Glu Asn Phe Leu Gln Thr
            525                 530                 535

AAG TAC GTC GGC CAG AAG CGC TTC TCC CTC GAA GGT GCA GAA GCT CTC        2104
Lys Tyr Val Gly Gln Lys Arg Phe Ser Leu Glu Gly Ala Glu Ala Leu
540                 545                 550

ATC CCA CTG ATG GAC TCC GCC ATC GAC ACC GCC GCA GGC CAG GGC CTC        2152
Ile Pro Leu Met Asp Ser Ala Ile Asp Thr Ala Ala Gly Gln Gly Leu
555                 560                 565                 570

GAC GAA GTT GTC ATC GGT ATG CCA CAC CGT GGT CGC CTC AAC GTG CTG        2200
Asp Glu Val Val Ile Gly Met Pro His Arg Gly Arg Leu Asn Val Leu
            575                 580                 585

TTC AAC ATC GTG GGC AAG CCA CTG GCA TCC ATC TTC AAC GAG TTT GAA        2248
Phe Asn Ile Val Gly Lys Pro Leu Ala Ser Ile Phe Asn Glu Phe Glu
                590                 595                 600

GGC CAA ATG GAG CAG GGC CAG ATC GGT GGC TCC GGT GAC GTG AAG TAC        2296
Gly Gln Met Glu Gln Gly Gln Ile Gly Gly Ser Gly Asp Val Lys Tyr
            605                 610                 615

CAC CTC GGT TCC GAA GGC CAG CAC CTG CAG ATG TTC GGC GAC GGC GAG        2344
His Leu Gly Ser Glu Gly Gln His Leu Gln Met Phe Gly Asp Gly Glu
620                 625                 630

ATC AAG GTC TCC CTG ACT GCT AAC CCG TCC CAC CTG GAA GCT GTT AAC        2392
Ile Lys Val Ser Leu Thr Ala Asn Pro Ser His Leu Glu Ala Val Asn
635                 640                 645                 650

CCA GTG ATG GAA GGT ATC GTC CGC GCA AAG CAG GAC TAC CTG GAC AAG        2440
Pro Val Met Glu Gly Ile Val Arg Ala Lys Gln Asp Tyr Leu Asp Lys
                655                 660                 665

GGC GTA GAC GGC AAG ACT GTT GTG CCA CTG CTC CTC CAC GGT GAC GCT        2488
Gly Val Asp Gly Lys Thr Val Val Pro Leu Leu Leu His Gly Asp Ala
            670                 675                 680

GCA TTC GCA GGC CTG GGC ATC GTG CCA GAA ACC ATC AAC CTG GCT AAG        2536
Ala Phe Ala Gly Leu Gly Ile Val Pro Glu Thr Ile Asn Leu Ala Lys
                685                 690                 695

CTG CGT GGC TAC GAC GTC GGA GGC ACC ATC CAC ATC GTG GTG AAC AAC        2584
Leu Arg Gly Tyr Asp Val Gly Gly Thr Ile His Ile Val Val Asn Asn
700                 705                 710

CAG ATC GGC TTC ACC ACC ACC CCA GAC TCC AGC CGC TCC ATG CAC TAC        2632
Gln Ile Gly Phe Thr Thr Thr Pro Asp Ser Ser Arg Ser Met His Tyr
715                 720                 725                 730

GCA ACC GAC TAC GCC AAG GCA TTC GGC TGC CCA GTC TTC CAC GTC AAT        2680
Ala Thr Asp Tyr Ala Lys Ala Phe Gly Cys Pro Val Phe His Val Asn
            735                 740                 745

GGT GAT GAC CCA GAG GCA GTT GTC TGG GTT GGC CAG CTG GCA ACC GAG        2728
Gly Asp Asp Pro Glu Ala Val Val Trp Val Gly Gln Leu Ala Thr Glu
                750                 755                 760

TAC CGT CGT CGC TTC GGC AAG GAC GTC TTC ATC GAC CTC GTT TGC TAC        2776
Tyr Arg Arg Arg Phe Gly Lys Asp Val Phe Ile Asp Leu Val Cys Tyr
            765                 770                 775
```

```
CGC CTC CGC GGC CAC AAC GAA GCT GAT GAT CCT TCC ATG ACC CAG CCA    2824
Arg Leu Arg Gly His Asn Glu Ala Asp Asp Pro Ser Met Thr Gln Pro
    780                 785                 790

AAG ATG TAT GAG CTC ATC ACC GGC CGC GAG ACC GTT CGT GCT CAG TAC    2872
Lys Met Tyr Glu Leu Ile Thr Gly Arg Glu Thr Val Arg Ala Gln Tyr
795                 800                 805                 810

ACC GAA GAC CTG CTC GGA CGT GGA GAC CTC TCC AAC GAA GAT GCA GAA    2920
Thr Glu Asp Leu Leu Gly Arg Gly Asp Leu Ser Asn Glu Asp Ala Glu
                815                 820                 825

GCA GTC GTC CGC GAC TTC CAC GAC CAG ATG GAA TCT GTG TTC AAC GAA    2968
Ala Val Val Arg Asp Phe His Asp Gln Met Glu Ser Val Phe Asn Glu
            830                 835                 840

GTC AAG GAA GGC GGC AAG AAG CAG GCT GAG GCA CAG ACC GGC ATC ACC    3016
Val Lys Glu Gly Gly Lys Lys Gln Ala Glu Ala Gln Thr Gly Ile Thr
        845                 850                 855

GGC TCC CAG AAG CTT CCA CAC GGC CTT GAG ACC AAC ATC TCC CGT GAA    3064
Gly Ser Gln Lys Leu Pro His Gly Leu Glu Thr Asn Ile Ser Arg Glu
    860                 865                 870

GAG CTC CTG GAA CTG GGA CAG GCT TTC GCC AAC ACC CCA GAA GGC TTC    3112
Glu Leu Leu Glu Leu Gly Gln Ala Phe Ala Asn Thr Pro Glu Gly Phe
875                 880                 885                 890

AAC TAC CAC CCA CGT GTG GCT CCA GTT GCT AAG AAG CGC GTC TCC TCT    3160
Asn Tyr His Pro Arg Val Ala Pro Val Ala Lys Lys Arg Val Ser Ser
                895                 900                 905

GTC ACC GAA GGT GGC ATC GAC TGG GCA TGG GGC GAG CTC CTC GCC TTC    3208
Val Thr Glu Gly Gly Ile Asp Trp Ala Trp Gly Glu Leu Leu Ala Phe
            910                 915                 920

GGT TCC CTG GCT AAC TCC GGC CGC TTG GTT CGC CTT GCA GGT GAA GAT    3256
Gly Ser Leu Ala Asn Ser Gly Arg Leu Val Arg Leu Ala Gly Glu Asp
        925                 930                 935

TCC CGC CGC GGT ACC TTC ACC CAG CGC CAC GCA GTT GCC ATC GAC CCA    3304
Ser Arg Arg Gly Thr Phe Thr Gln Arg His Ala Val Ala Ile Asp Pro
    940                 945                 950

GCG ACC GCT GAA GAG TTC AAC CCA CTC CAC GAG CTT GCA CAG TCC AAG    3352
Ala Thr Ala Glu Glu Phe Asn Pro Leu His Glu Leu Ala Gln Ser Lys
955                 960                 965                 970

GGC AAC AAC GGT AAG TTC CTG GTC TAC AAC TCC GCA CTG ACC GAG TAC    3400
Gly Asn Asn Gly Lys Phe Leu Val Tyr Asn Ser Ala Leu Thr Glu Tyr
                975                 980                 985

GCA GGC ATG GGC TTC GAG TAC GGC TAC TCC GTA GGA AAC GAA GAC TCC    3448
Ala Gly Met Gly Phe Glu Tyr Gly Tyr Ser Val Gly Asn Glu Asp Ser
            990                 995                 1000

GTC GTT GCA TGG GAA GCA CAG TTC GGC GAC TTC GCC AAC GGC GCT CAG    3496
Val Val Ala Trp Glu Ala Gln Phe Gly Asp Phe Ala Asn Gly Ala Gln
        1005                1010                1015

ACC ATC ATC GAT GAG TAC GTC TCC TCA GGC GAA GCT AAG TGG GGC CAG    3544
Thr Ile Ile Asp Glu Tyr Val Ser Ser Gly Glu Ala Lys Trp Gly Gln
    1020                1025                1030

ACC TCC AAG CTG ATC CTT CTG CTG CCT CAC GGC TAC GAA GGC CAG GGC    3592
Thr Ser Lys Leu Ile Leu Leu Leu Pro His Gly Tyr Glu Gly Gln Gly
1035                1040                1045                1050

CCA GAC CAC TCT TCC GCA CGT ATC GAG CGC TTC CTG CAG CTG TGC GCT    3640
Pro Asp His Ser Ser Ala Arg Ile Glu Arg Phe Leu Gln Leu Cys Ala
                1055                1060                1065

GAG GGT TCC ATG ACT GTT GCT CAG CCA TCC ACC CCA GCA AAC CAC TTC    3688
Glu Gly Ser Met Thr Val Ala Gln Pro Ser Thr Pro Ala Asn His Phe
            1070                1075                1080

CAC CTG CTG CGT CGT CAC GCT CTG TCC GAC CTG AAG CGT CCA CTG GTT    3736
His Leu Leu Arg Arg His Ala Leu Ser Asp Leu Lys Arg Pro Leu Val
        1085                1090                1095
```

```
ATC TTC ACC CCG AAG TCC ATG CTG CGT AAC AAG GCT GCT GCC TCC GCA    3784
Ile Phe Thr Pro Lys Ser Met Leu Arg Asn Lys Ala Ala Ala Ser Ala
    1100                1105                1110

CCA GAA GAC TTC ACT GAG GTC ACC AAG TTC CAA TCC GTG ATC GAC GAT    3832
Pro Glu Asp Phe Thr Glu Val Thr Lys Phe Gln Ser Val Ile Asp Asp
1115                1120                1125                1130

CCA AAC GTT GCA GAT GCA GCC AAG GTG AAG AAG GTC ATG CTG GTC TCC    3880
Pro Asn Val Ala Asp Ala Ala Lys Val Lys Lys Val Met Leu Val Ser
                1135                1140                1145

GGC AAG CTG TAC TAC GAA TTG GCA AAG CGC AAG GAG AAG GAC GGA CGC    3928
Gly Lys Leu Tyr Tyr Glu Leu Ala Lys Arg Lys Glu Lys Asp Gly Arg
            1150                1155                1160

GAC GAC ATC GCG ATC GTT CGT ATC GAA ATG CTC CAC CCA ATT CCG TTC    3976
Asp Asp Ile Ala Ile Val Arg Ile Glu Met Leu His Pro Ile Pro Phe
        1165                1170                1175

AAC CGC ATC TCC GAG GCT CTT GCC GGC TAC CCT AAC GCT GAG GAA GTC    4024
Asn Arg Ile Ser Glu Ala Leu Ala Gly Tyr Pro Asn Ala Glu Glu Val
    1180                1185                1190

CTC TTC GTT CAG GAT GAG CCA GCA AAC CAG GGC CCA TGG CCG TTC TAC    4072
Leu Phe Val Gln Asp Glu Pro Ala Asn Gln Gly Pro Trp Pro Phe Tyr
1195                1200                1205                1210

CAG GAG CAC CTC CCA GAG CTG ATC CCG AAC ATG CCA AAG ATG CGC CGC    4120
Gln Glu His Leu Pro Glu Leu Ile Pro Asn Met Pro Lys Met Arg Arg
                1215                1220                1225

GTT TCC CGC CGC GCT CAG TCC TCC ACC GCA ACT GGT GTT GCT AAG GTG    4168
Val Ser Arg Arg Ala Gln Ser Ser Thr Ala Thr Gly Val Ala Lys Val
            1230                1235                1240

CAC CAG CTG GAG GAG AAG CAG CTT ATC GAC GAG GCT TTC GAG GCT        4213
His Gln Leu Glu Glu Lys Gln Leu Ile Asp Glu Ala Phe Glu Ala
        1245                1250                1255

TAAGTCTTTA TAGTCCTGCA CTAGCCTAGA GGGCCTTATG CAGTGTGAAT CACACAGCAT   4273

AAGGCCCTTT TTGCTGCCGT GGTTGCCTAA GGTGGAAGGC ATGAAACGAA TCTGTGCGGT   4333

CACGATCTCT TCAGTACTTT TGCTAAGTGG CTGCTCCTCC ACTTCCACCA CGCAGCTCGA   4393

G                                                                   4394

(2) INFORMATION FOR SEQ ID NO:2:

(i) SEQUENCE CHARACTERISTICS:
        (A) LENGTH: 1257 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Gln Leu Gly Leu Arg His Asn Gln Pro Thr Thr Asn Val Thr
1               5                   10                  15

Val Asp Lys Ile Lys Leu Asn Lys Pro Ser Arg Ser Lys Glu Lys Arg
            20                  25                  30

Arg Val Pro Ala Val Ser Ser Ala Ser Thr Phe Gly Gln Asn Ala Trp
        35                  40                  45

Leu Val Asp Glu Met Phe Gln Gln Phe Gln Lys Asp Pro Lys Ser Val
    50                  55                  60

Asp Lys Glu Trp Arg Glu Leu Phe Glu Ala Gln Gly Gly Pro Asn Ala
65                  70                  75                  80

Thr Pro Ala Thr Thr Glu Ala Gln Pro Ser Ala Pro Lys Glu Ser Ala
                85                  90                  95

Lys Pro Ala Pro Lys Ala Ala Pro Ala Ala Lys Ala Ala Pro Arg Val
```

-continued

```
                100                 105                 110
Glu Thr Lys Pro Ala Ala Lys Thr Ala Pro Lys Ala Lys Glu Ser Ser
            115                 120                 125
Val Pro Gln Gln Pro Lys Leu Pro Glu Pro Gly Gln Thr Pro Ile Arg
130                 135                 140
Gly Ile Phe Lys Ser Ile Ala Lys Asn Met Asp Ile Ser Leu Glu Ile
145                 150                 155                 160
Pro Thr Ala Thr Ser Val Arg Asp Met Pro Ala Arg Leu Met Phe Glu
                165                 170                 175
Asn Arg Ala Met Val Asn Asp Gln Leu Lys Arg Thr Arg Gly Gly Lys
            180                 185                 190
Ile Ser Phe Thr His Ile Ile Gly Tyr Ala Met Val Lys Ala Val Met
        195                 200                 205
Ala His Pro Asp Met Asn Asn Ser Tyr Asp Val Ile Asp Gly Lys Pro
    210                 215                 220
Thr Leu Ile Val Pro Glu His Ile Asn Leu Gly Leu Ala Ile Asp Leu
225                 230                 235                 240
Pro Gln Lys Asp Gly Ser Arg Ala Leu Val Val Ala Ala Ile Lys Glu
                245                 250                 255
Thr Glu Lys Met Asn Phe Ser Glu Phe Leu Ala Ala Tyr Glu Asp Ile
            260                 265                 270
Val Thr Arg Ser Arg Lys Gly Lys Leu Thr Met Asp Asp Tyr Gln Gly
        275                 280                 285
Val Thr Val Ser Leu Thr Asn Pro Gly Gly Ile Gly Thr Arg His Ser
    290                 295                 300
Val Pro Arg Leu Thr Lys Gly Gln Gly Thr Ile Ile Gly Val Gly Ser
305                 310                 315                 320
Met Asp Tyr Pro Ala Glu Phe Gln Gly Ala Ser Glu Asp Arg Leu Ala
                325                 330                 335
Glu Leu Gly Val Gly Lys Leu Val Thr Ile Thr Ser Thr Tyr Asp His
            340                 345                 350
Arg Val Ile Gln Gly Ala Val Ser Gly Glu Phe Leu Arg Thr Met Ser
        355                 360                 365
Arg Leu Leu Thr Asp Asp Ser Phe Trp Asp Glu Ile Phe Asp Ala Met
    370                 375                 380
Asn Val Pro Tyr Thr Pro Met Arg Trp Ala Gln Asp Val Pro Asn Thr
385                 390                 395                 400
Gly Val Asp Lys Asn Thr Arg Val Met Gln Leu Ile Glu Ala Tyr Arg
                405                 410                 415
Ser Arg Gly His Leu Ile Ala Asp Thr Asn Pro Leu Ser Trp Val Gln
            420                 425                 430
Pro Gly Met Pro Val Pro Asp His Arg Asp Leu Asp Ile Glu Thr His
        435                 440                 445
Ser Leu Thr Ile Trp Asp Leu Asp Arg Thr Phe Ser Val Gly Gly Phe
    450                 455                 460
Gly Gly Lys Glu Thr Met Thr Leu Arg Glu Val Leu Ser Arg Leu Arg
465                 470                 475                 480
Ala Ala Tyr Thr Leu Lys Val Gly Ser Glu Tyr Thr His Ile Leu Asp
                485                 490                 495
Arg Asp Glu Arg Thr Trp Leu Gln Asp Arg Leu Glu Ala Gly Met Pro
            500                 505                 510
Lys Pro Thr Gln Ala Glu Gln Lys Tyr Ile Leu Gln Lys Leu Asn Ala
        515                 520                 525
```

```
Ala Glu Ala Phe Glu Asn Phe Leu Gln Thr Lys Tyr Val Gly Gln Lys
530                 535                 540

Arg Phe Ser Leu Glu Gly Ala Glu Ala Leu Ile Pro Leu Met Asp Ser
545                 550                 555                 560

Ala Ile Asp Thr Ala Gly Gln Gly Leu Asp Glu Val Val Ile Gly
                565                 570                 575

Met Pro His Arg Gly Arg Leu Asn Val Leu Phe Asn Ile Val Gly Lys
                580                 585                 590

Pro Leu Ala Ser Ile Phe Asn Glu Phe Glu Gly Gln Met Glu Gln Gly
                595                 600                 605

Gln Ile Gly Gly Ser Gly Asp Val Lys Tyr His Leu Gly Ser Glu Gly
                610                 615                 620

Gln His Leu Gln Met Phe Gly Asp Gly Glu Ile Lys Val Ser Leu Thr
625                 630                 635                 640

Ala Asn Pro Ser His Leu Glu Ala Val Asn Pro Val Met Glu Gly Ile
                645                 650                 655

Val Arg Ala Lys Gln Asp Tyr Leu Asp Lys Gly Val Asp Gly Lys Thr
                660                 665                 670

Val Val Pro Leu Leu Leu His Gly Asp Ala Ala Phe Ala Gly Leu Gly
                675                 680                 685

Ile Val Pro Glu Thr Ile Asn Leu Ala Lys Leu Arg Gly Tyr Asp Val
                690                 695                 700

Gly Gly Thr Ile His Ile Val Asn Asn Gln Ile Gly Phe Thr Thr
705                 710                 715                 720

Thr Pro Asp Ser Ser Arg Ser Met His Tyr Ala Thr Asp Tyr Ala Lys
                725                 730                 735

Ala Phe Gly Cys Pro Val Phe His Val Asn Gly Asp Asp Pro Glu Ala
                740                 745                 750

Val Val Trp Val Gly Gln Leu Ala Thr Glu Tyr Arg Arg Arg Phe Gly
                755                 760                 765

Lys Asp Val Phe Ile Asp Leu Val Cys Tyr Arg Leu Arg Gly His Asn
770                 775                 780

Glu Ala Asp Asp Pro Ser Met Thr Gln Pro Lys Met Tyr Glu Leu Ile
785                 790                 795                 800

Thr Gly Arg Glu Thr Val Arg Ala Gln Tyr Thr Glu Asp Leu Leu Gly
                805                 810                 815

Arg Gly Asp Leu Ser Asn Glu Asp Ala Glu Ala Val Val Arg Asp Phe
                820                 825                 830

His Asp Gln Met Glu Ser Val Phe Asn Glu Val Lys Glu Gly Gly Lys
                835                 840                 845

Lys Gln Ala Glu Ala Gln Thr Gly Ile Thr Gly Ser Gln Lys Leu Pro
850                 855                 860

His Gly Leu Glu Thr Asn Ile Ser Arg Glu Glu Leu Glu Leu Gly
865                 870                 875                 880

Gln Ala Phe Ala Asn Thr Pro Glu Gly Phe Asn Tyr His Pro Arg Val
                885                 890                 895

Ala Pro Val Ala Lys Lys Arg Val Ser Ser Val Thr Glu Gly Gly Ile
                900                 905                 910

Asp Trp Ala Trp Gly Glu Leu Leu Ala Phe Gly Ser Leu Ala Asn Ser
                915                 920                 925

Gly Arg Leu Val Arg Leu Ala Gly Glu Asp Ser Arg Arg Gly Thr Phe
                930                 935                 940

Thr Gln Arg His Ala Val Ala Ile Asp Pro Ala Thr Ala Glu Glu Phe
945                 950                 955                 960
```

```
Asn Pro Leu His Glu Leu Ala Gln Ser Lys Gly Asn Asn Gly Lys Phe
            965                 970                 975
Leu Val Tyr Asn Ser Ala Leu Thr Glu Tyr Ala Gly Met Gly Phe Glu
            980                 985                 990
Tyr Gly Tyr Ser Val Gly Asn Glu Asp Ser Val Val Ala Trp Glu Ala
            995                 1000                1005
Gln Phe Gly Asp Phe Ala Asn Gly Ala Gln Thr Ile Ile Asp Glu Tyr
            1010                1015                1020
Val Ser Ser Gly Glu Ala Lys Trp Gly Gln Thr Ser Lys Leu Ile Leu
025                 1030                1035                1040
Leu Leu Pro His Gly Tyr Glu Gly Gln Gly Pro Asp His Ser Ser Ala
            1045                1050                1055
Arg Ile Glu Arg Phe Leu Gln Leu Cys Ala Glu Gly Ser Met Thr Val
            1060                1065                1070
Ala Gln Pro Ser Thr Pro Ala Asn His Phe His Leu Leu Arg Arg His
            1075                1080                1085
Ala Leu Ser Asp Leu Lys Arg Pro Leu Val Ile Phe Thr Pro Lys Ser
            1090                1095                1100
Met Leu Arg Asn Lys Ala Ala Ala Ser Ala Pro Glu Asp Phe Thr Glu
105                 1110                1115                1120
Val Thr Lys Phe Gln Ser Val Ile Asp Asp Pro Asn Val Ala Asp Ala
            1125                1130                1135
Ala Lys Val Lys Lys Val Met Leu Val Ser Gly Lys Leu Tyr Tyr Glu
            1140                1145                1150
Leu Ala Lys Arg Lys Glu Lys Asp Gly Arg Asp Asp Ile Ala Ile Val
            1155                1160                1165
Arg Ile Glu Met Leu His Pro Ile Pro Phe Asn Arg Ile Ser Glu Ala
    1170                1175                1180
Leu Ala Gly Tyr Pro Asn Ala Glu Glu Val Leu Phe Val Gln Asp Glu
185                 1190                1195                1200
Pro Ala Asn Gln Gly Pro Trp Pro Phe Tyr Gln Glu His Leu Pro Glu
            1205                1210                1215
Leu Ile Pro Asn Met Pro Lys Met Arg Arg Val Ser Arg Arg Ala Gln
            1220                1225                1230
Ser Ser Thr Ala Thr Gly Val Ala Lys Val His Gln Leu Glu Glu Lys
            1235                1240                1245
Gln Leu Ile Asp Glu Ala Phe Glu Ala
            1250                1255

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: NO (xi) SEQUENCE DESCRIPTION: SEQ ID NO:3:

CTGTCTGAAG GATCGGTTCT                                                  20

(2) INFORMATION FOR SEQ ID NO:4:
```

(i) SEQUENCE CHARACTERISTICS:
    (A) LENGTH: 29 base pairs
    (B) TYPE: nucleic acid
    (C) STRANDEDNESS: single
    (D) TOPOLOGY: linear (ii) MOLECULE TYPE: Other nucleic acid
    (A) DESCRIPTION: /desc="Synthetic DNA"

(iii) HYPOTHETICAL: NO (iv) ANTI-SENSE: YES (xi) SEQUENCE DESCRIPTION: SEQ ID NO:4:

GAGTGCTCAG GCCCCTGTCC CTCGTAACC                     29

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: NO (xi) SEQUENCE DESCRIPTION: SEQ ID NO:5:

GCTAGCCTCG GGAGCTCTAG                               20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: YES (xi) SEQUENCE DESCRIPTION: SEQ ID NO:6:

GATCTTTCCC AGACTCTGGC                               20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: NO (xi) SEQUENCE DESCRIPTION: SEQ ID NO:7:

TAATGCCACC GACACCCACC                               20

(2) INFORMATION FOR SEQ ID NO:8:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: YES (xi) SEQUENCE DESCRIPTION: SEQ ID NO:8:

TCAACGCCCA CATAGTGGAC                                          20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: NO (xi) SEQUENCE DESCRIPTION: SEQ ID NO:9:

GAATTCGCTC CCGGTGACGC                                          20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: YES (xi) SEQUENCE DESCRIPTION: SEQ ID NO:10:

GATGCAGAAT TCCTTGTCGG                                          20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid
        (A) DESCRIPTION: /desc="Synthetic DNA"

(iii) HYPOTHETICAL: NO (iv) ANTI-SENSE: NO (xi) SEQUENCE DESCRIPTION: SEQ ID NO:11:

GTCGACGGCG GACTTGTCGG                                          20

(2) INFORMATION FOR SEQ ID NO:12:
```

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: /desc="Synthetic DNA"

(iii) HYPOTHETICAL: NO (iv) ANTI-SENSE: YES (xi) SEQUENCE DESCRIPTION: SEQ ID NO:12:

GTCGACAAAA CCCAAAAAAA                                                        20

(2) INFORMATION FOR SEQ ID NO:13:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: /desc="Synthetic DNA"

(iii) HYPOTHETICAL: NO (iv) ANTI-SENSE: NO (xi) SEQUENCE DESCRIPTION: SEQ ID NO:13:

CTGCGGAAAC TACACAAGAA CCCAAAAATG ATTAATAATT GAGACAAGCT T                     51

(2) INFORMATION FOR SEQ ID NO:14:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: Other nucleic acid
            (A) DESCRIPTION: /desc="Synthetic DNA"

(iii) HYPOTHETICAL: NO (iv) ANTI-SENSE: YES (xi) SEQUENCE DESCRIPTION: SEQ ID NO:14:

CTAGAAGCTT GTCTCAATTA TTAATCATTT TTGGGTTCTT GTGTAGTTTC CGCAGGTAC             59